US009066906B2

(12) United States Patent
Davis et al.

(10) Patent No.: US 9,066,906 B2
(45) Date of Patent: Jun. 30, 2015

(54) LUNASIN-CONTAINING COMPLEX AND PURIFICATION OF LUNASIN FROM PLANTS

(75) Inventors: Keith Davis, Owensboro, KY (US); Brian Barnett, Owensboro, KY (US); Jian Cai, Louisville, KY (US); Elizabeth McConnell, Owensboro, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 84 days.

(21) Appl. No.: 13/509,547

(22) PCT Filed: Nov. 11, 2010

(86) PCT No.: PCT/US2010/056398
§ 371 (c)(1),
(2), (4) Date: May 11, 2012

(87) PCT Pub. No.: WO2011/060181
PCT Pub. Date: May 19, 2011

(65) Prior Publication Data
US 2012/0220538 A1 Aug. 30, 2012

Related U.S. Application Data

(60) Provisional application No. 61/260,064, filed on Nov. 11, 2009.

(51) Int. Cl.
A61K 38/16 (2006.01)

(52) U.S. Cl.
CPC .................................... A61K 38/168 (2013.01)

(58) Field of Classification Search
None
See application file for complete search history.

(56) References Cited

U.S. PATENT DOCUMENTS

| 6,107,287 | A | 8/2000 | de Lumen et al. | |
|---|---|---|---|---|
| 6,391,848 | B1 * | 5/2002 | de Lumen et al. | 514/21.6 |
| 6,544,956 | B1 | 4/2003 | de Lumen et al. | |
| 7,192,615 | B2 | 3/2007 | Liu et al. | |
| 7,309,688 | B2 | 12/2007 | Seiberg et al. | |
| 7,375,092 | B2 | 5/2008 | de Lumen et al. | |
| 7,404,973 | B2 | 7/2008 | Konwinski et al. | |
| 7,731,995 | B2 | 6/2010 | Galvez | |
| 8,759,613 | B1 * | 6/2014 | Davis et al. | 800/288 |
| 2003/0027765 | A1 | 2/2003 | Galvez | |
| 2003/0064121 | A1 | 4/2003 | Konwinski et al. | |
| 2003/0224420 | A1 | 12/2003 | Hellerstein et al. | |
| 2003/0229038 | A1 | 12/2003 | de Lumen et al. | |
| 2007/0054031 | A1 * | 3/2007 | Liu | 426/634 |
| 2007/0292494 | A1 | 12/2007 | Gieseler et al. | |
| 2008/0003567 | A1 | 1/2008 | Rodriguez et al. | |
| 2008/0070827 | A1 | 3/2008 | Galvez | |
| 2010/0092497 | A1 | 4/2010 | Kanwar et al. | |
| 2010/0197594 | A1 | 8/2010 | Galvez | |
| 2012/0220538 | A1 * | 8/2012 | Davis et al. | 514/19.3 |

FOREIGN PATENT DOCUMENTS

WO 2001034808 A2 5/2001

OTHER PUBLICATIONS

Dia et al. ("Isolation, purification and characterization of lunasin from defatted soybean flour and in vitro evaluation of its anti-inflammatory activity". Food Chem, May 2009, vol. 114, No. 1, p. 108-115).*
Ampe et al., "The amino-acid sequence of the 2S sulphur-rich proteins from seeds of Brazil nut (Bertholletia excelsa H.B.K.)," Eur. J. Biochem., 1986, vol. 159, pp. 597-604.
Balasubramanyam et al., "Curcumin, a novel p300/CREB-binding protein-specific inhibitor of acetyltransferase, represses the acetylation of histone/nonhistone proteins and histone acetyltransferase-dependent chromatin transcription," J Biol Chem., 2004, vol. 279(49), pp. 51163-51171.
Chiesa et al., "Reduced mammary tumor progression in a transgenic mouse model fed an isoflavone-poor soy protein concentrate," Mol Nutr Food Res, 2008, vo. 52(10), pp. 1121-1129.
De Lumen, B.O., "Lunasin: a novel cancer preventive seed peptide that modifies chromatin," J AOAC Int, 2008, vol. 91(4), pp. 932-935.
De Lumen, B.O., "Lunasin: a cancer-preventive soy peptide," Nutr Rev, 2005, vol. 63(1), pp. 16-21.
De Mejia et al., "Lunasin, with an arginine-glycine-aspartic acid motif, causes apoptosis to L1210 leukemia cells by activation of caspase-3," Mol Nutr Food Res, 2010, vol. 54(3), pp. 406-414.
De Mejia et al., "Lunasin and lunasin-like peptides inhibit inflammation through suppression of NF-kappaB pathway in the macrophage," Peptides, 2009, vol. 30(12), pp. 2388-2398.
De Mejia et al., "The anticarcinogenic potential of soybean lectin and lunasin," Nutr Rev, 2003, vol. 61(7), pp. 239-246.
Dia et al., "Lunasin promotes apoptosis in human colon cancer cells by mitochondrial pathway activation and induction of nuclear clusterin expression," Cancer Lett, 2010, vol. 295(1), pp. 44-53.
Dia et al., "Presence of lunasin in plasma of men after soy protein consumption," J Agric Food Chem, 2009, vol. 57, pp. 1260-1266.

(Continued)

Primary Examiner — Maury Audet
(74) Attorney, Agent, or Firm — Stites & Harbison PLLC; Mandy Wilson Decker

(57) ABSTRACT

A method of purifying lunasin or a lunasin-containing complex produced in a plant includes providing a plant material from the plant, and isolating the lunasin-containing complex from the plant material, and/or releasing lunasin from the lunasin-containing complex. A composition for treating a cancer or an inflammation-related disease in a subject includes a lunasin-containing complex. A composition for treating a cancer or an inflammation-related disease in a subject includes a lunasin polypeptide and/or a lunasin-containing complex; and curcumin, wherein the combination of the a lunasin polypeptide or lunasin-containing complex and the curcumin has a synergistic effect. A method for treating a cancer or an inflammation-related disease includes administering a composition including a lunasin-containing complex, or a lunasin polypeptide and/or a lunasin-containing complex, and curcumin.

18 Claims, 7 Drawing Sheets

(56) References Cited

OTHER PUBLICATIONS

Dia et al., Isolation, purification and characterization of lunasin from defatted soybean flour and in vitro evaluation of its anti-inflammatory activity, Food Chemistry, 2009, vol. 114, pp. 108-115.
Dia et al., "Bowman-Birk inhibitor and genistein among soy compounds that synergistically inhibit nitric oxide and prostaglandin E2 pathways in lipopolysaccharide-induced macrophages," J Agric Food Chem, 2008, vol. 56(24), pp. 11707-11717.
Elayadi AN, et al. (2007). A peptide selected by biopanning identifies the integrin alphavbeta6 as a prognostic biomarker for nonsmall cell lung cancer. Cancer Res. 67(12):5889-95.
Ericson et al., "Structure of the Rapeseed 1.7 S Storage Protein, Napin, and its Precursor," J Biological Chem, 1986, vol. 261, pp. 14576-14581.
Fullwood et al., "ChIP-based methods for the identification of long-range chromatin interactions," J Cell Biochem, 2009, vol. 107(1), pp. 30-39.
Galvez et al., "Chemopreventive property of a soybean peptide (lunasin) that binds to deacetylated histones and inhibits acetylation," Cancer Res, 2001, vol. 61, pp. 7473-7478.
Galvez et al., "A soybean cDNA encoding a chromatin-binding peptide inhibits mitosis of mammalian cells," Nat Biotechnol, 1999, vol. 17, pp. 495-500.
Go et al., "Diet, nutrition and cancer prevention: where are we going from here?," J Nutr, 2001, vol. 131(11 Suppl), pp. 3121S-3126S.
Gonzalez et al., "Lunasin concentration in different soybean genotypes, commercial soy protein, and isoflavone products," J Agric Food Chem, 2004, vol. 52(19), pp. 5882-5887.
Hernandez-Ledesma et al., "Antioxidant and anti-inflammatory properties of cancer preventive peptide lunasin in RAW 264.7 macrophages," Biochem Biophys Res Commun, 2009, vol. 390(3), pp. 803-808.
Hernandez-Ledesma et al., "Lunasin, a novel seed peptide for cancer prevention," Peptides, 2009, vol. 30(2), pp. 426-430.
Hernandez-Ledesma et al., "Lunasin, a novel cancer preventive peptide," Perspect Medicin Chem, 2008, vol. 2, pp. 75-80.
Hsieh et al., "Lunasin, a novel seed peptide, sensitizes human breast cancer MDA-MB-231 cells to aspirin-arrested cell cycle and induced apoptosis," Chem Biol Interact, 2010a, vol. 186(2), pp. 127-134.
Hsieh et al., "Complementary roles in cancer prevention: protease inhibitor makes the cancer preventive peptide lunasin bioavailable," PLoS One, 2010b, vol. 5(1), p. e8890.
Hsieh et al., "Dynamics of keratinocytes in vivo using HO labeling: a sensitive marker of epidermal proliferation state," J Invest Dermatol, 2004, vol. 123(3), pp. 530-536.
Hu et al., "Curcumin-induced histone acetylation in malignant hematologic cells," J Huazhong Univ Sci Technolog Med Sci, 2009, vol. 29(1), pp. 25-28.
Jeong et al., "The cancer preventive seed peptide lunasin from rye is bioavailable and bioactive," Nutr Cancer, 2009, vol. 61(5), pp. 680-686.
Jeong et al., "The cancer preventive peptide lunasin from wheat inhibits core histone acetylation," Cancer Lett, 2007b, vol. 255, pp. 42-48.
Jeong et al., "Inhibition of core histone acetylation by the cancer preventive peptide lunasin," J Agric Food Chem, 2007a, vol. 55, pp. 632-637.
Jeong et al., "Characterization of lunasin isolated from soybean," J Agric Food Chem, 2003, vol. 51, pp. 7901-7906.
Jeong et al., "Barley lunasin suppresses ras-induced colony formation and inhibits core histone acetylation in mammalian cells," J Agric Food Chem, 2002, vol. 50, pp. 5903-5908.
Jeong et al., "Lunasin peptide purified from *Solanum nigrum* L. protects DNA from oxidative damage by suppressing the generation of hydroxyl radical via blocking fenton reaction", Cancer Lett, 2010, vol. 293(1), pp. 58-64.
Kang et al., "Curcumin-induced histone hypoacetylation enhances caspase-3-dependent glioma cell death and neurogenesis of neural progenitor cells," Stem Cells Dev, 2006, vol. 15(2), pp. 165-174.
Krebbers et al., "Determination of the Processing Sites of an *Arabidopisis* 2S Albumin and Characterization of the Complete Gene Family," Plant Physiol, 1988, vol. 81, pp. 859-866.
Lam et al., "Lunasin suppresses E1A-mediated transformation of mammalian cells but does not inhibit growth of immortalized and established cancer cell lines," Nutr Cancer, 2003, vol. 47, pp. 88-94.
Li et al., "Synthesis and characterization of a high-affinitiy αvβ6-specific ligand for in vitro and in vivo applications," Mol. Cancer. Ther., 2009, vol. 8(5), pp. 1239-1248.
Lin et al., "The expression and processing of two recombinant 2S albumins from soybean (*Glycine max*) in the yeast *Pichia pastor's*," Biochimica et Biophysica Acta, 2004, vol. 1698, pp. 203-212.
Liu et al., Recombinant expression of bioactive peptide lunasin in *Escherichia coli*. Appl Microbiol Biotechnol, 2010, vol. 88, pp. 177-186.
Maldonado-Cervantes et al., Amaranth lunasin-like peptide internalizes into the cell nucleus and inhibits chemical carcinogen-induced transformation of NIH-3T3 cells, Peptides, 2010, doi: 10.1016/j.peptides.2010.06.014.
Martin et al., "High-yield, in vitro protein expression using a continuous-exchange, coupled transcription/translation system," Biotechniques, 2001, vol. 31(4), pp. 948-950, 952-3.
Odani et al., "Amino Acid Sequence of a Soybean (*Glycine max*) Seed Polypeptide Having a Poly(L-Aspartic Acid) Structure," The Journal of Biological Chemistry, 1987, vol. 262, pp. 10502-10505.
Omoni et al., "Soybean Foods and Their Benefits: Potential Mechanisms of Action," Nutrition Reviews, 2005, vol. 63 (8), pp. 272-283.
Park et al., "In vitro digestibility of the cancer-preventive soy peptides lunasin and BBI," J Agric Food Chem, 2007, vol. 55, pp. 10703-10706.
Park et al., "Contents and bioactivities of lunasin, bowman-birk inhibitor, and isoflavones in soybean seed," J Agric Food Chem, 2005, vol. 53, pp. 7686-7690.
Rodriguez et al., "Tilling the chromatin landscape: emerging methods for the discovery and profiling of protein-DNA interactions," Biochem Cell Biol, 2005, vol. 83(4), pp. 525-534.
Seber et al., "Scalable Purification and Characterization of the Anticancer Lunasin Peptide from Soybean," PLoS One, 2012, vol. 7(4), pp. 1-13, e35409.
Silva-Sanchez et al., "Bioactive peptides in amaranth (*Amaranthus hypochondriacus*) seed," J Agric Food Chem, 2008, vol. 56(4), pp. 1233-1240.
Wang et al., "Analysis of soybean protein-derived peptides and the effect of cultivar, environmental conditions, and processing on lunasin concentration in soybean and soy products," J AOAC Int, 2008b, vol. 91, pp. 936-946.
Wang et al., "beta-Conglycinins among sources of bioactives in hydrolysates of different soybean varieties that inhibit leukemia cells in vitro," J Agric Food Chem, 2008a, vol. 56, pp. 4012-4020.
De Mejia et al., "Soybean bioactive peptides: A new horizon in preventing chronic diseases," Sexuality Reproduction and Menopause, 2006, vol. 4(2), pp. 91-95.
Jeong et al., "Cancer-preventive peptide lunasin from *Solanum nigrum* L. inhibits acetylation of core histones H3 and H4 and phosphorylation of retinoblastoma protein (Rb)," J Agric Food Chem, 2007c, vol. 55(26), pp. 10707-10713.
USPTO/ISA, International Search Report and Written Opinion in corresponding international application PCT/ US10/56398, completed Feb. 20, 2011.

* cited by examiner

LUNASIN-CONTAINING COMPLEX AND PURIFICATION OF LUNASIN FROM PLANTS

RELATED APPLICATIONS

This application claims priority from U.S. Provisional Application Ser. No. 61/260,064 filed Nov. 11, 2009, the entire disclosure of which is incorporated herein by this reference.

GOVERNMENT INTEREST

This invention was made with government support under grant number W81XWH-09-2-0022 awarded by the United States Army. The United States government has certain rights in the invention.

TECHNICAL FIELD

The presently-disclosed subject matter relates to a method of obtaining lunasin from plants. In particular, the presently-disclosed subject matter relates to a method of producing the lunasin-containing complex and/or lunasin by purifying wild-type lunasin from plant material containing lunasin, such as soybean material.

INTRODUCTION

Wild-type lunasin from soybean is a polypeptide having 43-44 amino acids with a C-terminal end of nine consecutive aspartic acid residues derived from the post-translational processing of a 2S albumin protein encoded by the Gm2S gene. Lunasin was originally isolated from soybean but has been reported to have been found in a variety of plant species at relatively low levels.

Studies have demonstrated that lunasin can prevent the transformation of mammalian cells by chemical carcinogens or viral oncogenes. However, the initial published studies indicated that lunasin has little effect on normal or established cancer cell lines. Recent studies have shown that lunasin does inhibit the proliferation of specific cancer cell lines. This chemopreventive effect on cells undergoing a transformation event is thought to be mediated by the binding of lunasin to deacetylated core histones and/or exerting its effects via an epigenetic mechanism that disrupts the normal dynamics of histone acetylation-deacetylation.

Although the potential cancer-chemopreventive activity of lunasin has been known for almost a decade, little progress has been made to demonstrate clinical relevance because of limitations on the ability to produce sufficient quantities of lunasin at an effective cost to conduct large-scale animal studies and human clinical trials.

Accordingly, there remains a need in the art for a cost-effective method of producing lunasin on a larger scale than via currently-available techniques.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method of purifying lunasin or a lunasin-containing complex produced in a plant, including (a) providing a plant material from the plant; and (b) isolating the lunasin-containing complex from the plant material; and/or releasing lunasin from the lunasin-containing complex.

In some embodiments, the method also includes extracting the plant material. In some embodiments, the plant material is extracted using water or an aqueous solution. In some embodiments, the plant material is extracted using PBS.

In some embodiments, the plant is a soybean plant. In some embodiments, the plant material is a soy-based material containing a lunasin-containing complex. In some embodiments, the plant material is a soybean material obtained as a byproduct of soybean processing. In some embodiments, the soybean material is de-fatted soy flour or white flake. In some embodiments, the plant material is a hydrated plant material or an extracted plant material.

In some embodiments, releasing lunasin from the lunasin-containing complex comprises contacting the plant material with a reducing agent. In some embodiments, the reducing agent is selected from: β-mercaptoethanol (BME), dithiothreitol (DTT), tris(2-carboxyethyl)phosphine (TCEP), and 2-aminoethanethiol. In some embodiments, the reducing agent is BME at a concentration of about 100 mM to about 1.5 M. In some embodiments, the reducing agent is DTT at concentration of about 1 mM to about 2 mM. In some embodiments, the reducing agent is TCEP at a concentration of about 3 mM to about 100 mM.

In some embodiments, the method includes isolating the lunasin-containing complex from the plant material, and releasing lunasin from the lunasin-containing complex. In some embodiments, isolating the lunasin-containing complex comprises using a technique selected from a size-based filtration technique; a charge-based filtration technique; a hydrophobicity-based filtration technique; or a combination thereof. In some embodiments, isolating the lunasin-containing complex comprises subjecting the plant material to ultrafiltration and collecting the permeate. In some embodiments, a 50 kD molecular-weight cutoff membrane is used for ultrafiltration.

In some embodiments, the method also includes purifying the released lunasin. In some embodiments, the lunasin is purified using a technique selected from: a size-based filtration technique; a charge-based filtration technique; a hydrophobicity-based filtration technique; or a combination thereof.

The presently-disclosed subject matter includes a kit for purifying lunasin or a lunasin-containing complex produced in a plant. In some embodiments, the kit includes an extraction solution; and a device useful for purifying and/or concentrating lunasin or the lunasin-containing complex, said device selected from the group consisting of: a device for performing size-based filtration; a device for performing charge-based filtration; and a device for performing hydrophobicity-based filtration technique. In some embodiments, the kit also includes a reducing agent.

The presently-disclosed subject matter includes a method for treating a cancer or an inflammation-related disease, including administering a composition that includes a polypeptide complex, comprising a lunasin polypeptide, and a second polypeptide linked to the lunasin polypeptide by a disulfide bridge. In some embodiments, the lunasin polypeptide comprises an amino acid sequence selected from the group consisting of the sequence of SEQ ID NO: 1 and the sequence of SEQ ID NO: 2. In some embodiments, the second polypeptide comprises the sequence of SEQ ID NO: 3.

The presently-disclosed subject matter includes a kit for use in the treatment of a cancer or an inflammation-related disease, including a vial containing a purified polypeptide complex, comprising a lunasin polypeptide, and a second polypeptide linked to the lunasin polypeptide by a disulfide bridge. In some embodiments, the kit also includes means for administering the purified contents of the vial or vials.

The presently-disclosed subject matter includes a composition for treating a cancer or an inflammation-related disease in a subject including: (a) a lunasin polypeptide and/or a lunasin-containing complex; and (b) curcumin, wherein the combination of the a lunasin polypeptide or lunasin-containing complex and the curcumin has a synergistic effect. The presently-disclosed subject matter includes a method for treating a cancer or an inflammation-related disease, comprising administering a composition including: (a) a lunasin polypeptide and/or a lunasin-containing complex; and (b) curcumin, wherein the combination of the a lunasin polypeptide or lunasin-containing complex and the curcumin has a synergistic effect.

The presently-disclosed subject matter includes a kit including a vial containing a purified lunasin polypeptide or lunasin-containing complex, and curcumin; or packaged together, a first vial containing a purified lunasin polypeptide or lunasin-containing complex, and a second vial containing curcumin. In some embodiments, the kit also includes means for administering the purified contents of the vial or vials.

BRIEF DESCRIPTION OF THE SEQUENCE LISTING

Figure 1:
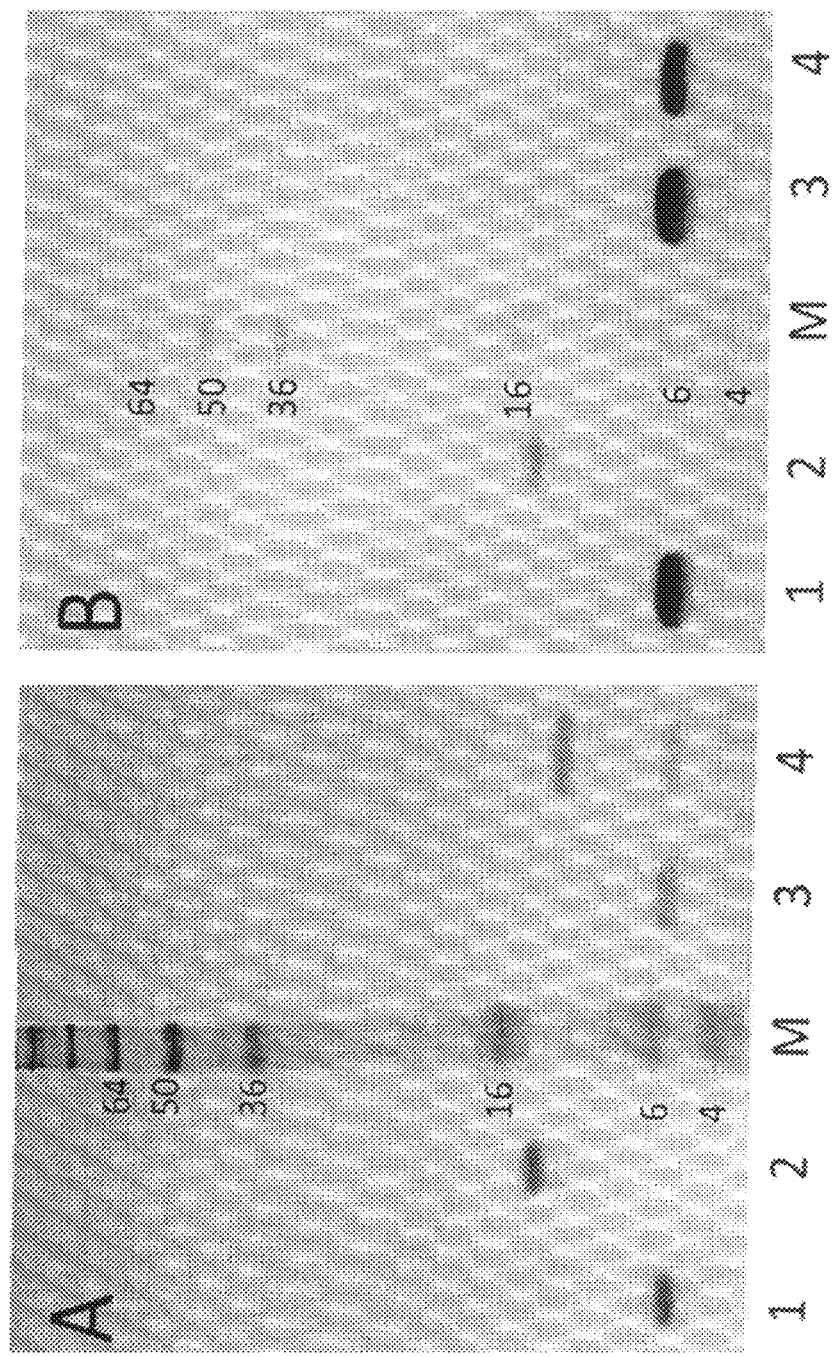
FIG. 1 is an image of a sodium dodecyl sulfate polyacrylamide gel electrophoresis (SDS-PAGE) gel and a corresponding immunoblot that characterizes a lunasin-containing complex from which lunasin can be obtained by treatment with a reducing agent.

SEQ ID NO: 1 is an amino acid sequence of a lunasin polypeptide.

SEQ ID NO: 2 is an amino acid sequence of a unique lunasin polypeptide of the presently-disclosed subject matter.

SEQ ID NO: 3 is an amino acid sequence of a second polypeptide that is included in some embodiments with a lunasin polypeptide, such as the lunasin polypeptide of SEQ ID NO: 1 or SEQ ID NO: 2, to form a lunasin-containing complex in which the lunasin polypeptide and the second polypeptide are covalently bonded via disulfide bridges.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used-herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is related to the surprising discovery that most (e.g., about 80-90%) of the lunasin found in plant material is covalently linked in a complex with another protein ("lunasin-containing complex"), while only a small portion of lunasin exists apart from the lunasin-containing complex as free-lunasin. The presently-disclosed subject matter is also related to the surprising discovery that a reducing agent can be used to release the lunasin from the lunasin-containing complex, allowing for a substantial increase in yields of lunasin that can be purified from plant material. Without wishing to be bound by theory, it is believed that prior attempts to purify lunasin from plants were unable to produce large yields because the attempts were directed towards purification of free-lunasin, while the lunasin-containing complex including most of the lunasin was discarded. To the extent that prior attempts to purify lunasin from plants had involved use of SDS-PAGE gels for identifying components of protein extracts obtained from plant materials, the lunasin-containing complex would have been disrupted because the typical protocol for preparing a protein sample for analysis by SDS-PAGE includes exposing the sample to a reducing agent, e.g., beta-mercaptoethanol (BME). As such, those who previously attempted to purify lunasin from plant material would not have been aware of, nor would they have sought to isolate, the lunasin-containing complex described in this application from the plant material. Rather, the plant extracts containing the lunasin-containing complex would have been discarded, in favor of pursuing purification of the free-lunasin found in the plant extract.

The presently-disclosed subject matter includes a method for larger-scale purification of lunasin from a plant and a kit for purifying lunasin from a plant. The purified lunasin can be used, for example, in a composition useful for treating a cancer or inflammation-related diseases. The presently-disclosed subject matter further includes a lunasin-containing complex, and method for making the lunasin-containing complex. The lunasin-containing complex is also biologically active and can have a greater activity than wild-type lunasin. The presently-disclosed subject matter further includes a kit including the lunasin-containing complex and means for administering the lunasin-containing complex to a subject. The presently-disclosed subject matter further includes a method of treating a cancer or inflammation-related disease in a subject, including administration of the lunasin-containing complex. The presently-disclosed subject matter further includes a composition including lunasin and/or lunasin-containing complex and curcumin, useful for treating a cancer or inflammation-related disease in a subject. The presently-disclosed subject matter further includes a kit including lunasin and/or lunasin-containing complex and curcumin. The presently-disclosed subject matter further includes a method of treating a cancer in a subject, including administration of lunasin and/or lunasin-containing complex and curcumin.

As used herein, lunasin refers to a wild-type lunasin that is produced in a plant. In some embodiments, the plant is a soybean plant (*Glycine max*). In some embodiments, the lunasin is a polypeptide having 43-44 amino acids. In some embodiments, the lunasin is a polypeptide having the sequence of SEQ ID NO: 1 (S-K-W-Q-H-Q-Q-D-S-C-R-K-Q-L-Q-G-V-N-L-T-P-C-E-K-H-I-M-E-K-I-Q-G-R-G-D-D-D-D-D-D-D-D-D). In some embodiments, the lunasin is a polypeptide having the sequence of SEQ ID NO: 2 (S-K-W-Q-H-Q-Q-D-S-C-R-K-Q-L-Q-G-V-N-L-T-P-C-E-K-H-I-M-E-K-I-Q-G-R-G-D-D-D-D-D-D-D-D-D-N). In some embodiments, the lunasin-containing complex or lunasin complex is a protein complex containing two polypeptides. For example, the first polypeptide can be a lunasin polypeptide having an amino acid sequence comprising the sequence of either SEQ ID NO: 1 or SEQ ID NO: 2, and the second polypeptide can have an amino acid sequence comprising the sequence of SEQ ID NO: 3 (E-G-K-D-E-D-E-E-E-E-G-H-M-Q-K-C-C-T-E-M-S-E-L-R-S-P-K-C-Q-C-K-A-L-Q-K-I-M-E-N-Q-S-E-E-L-E-E-K-Q-K-K-K-M-E-K-E-L-I-N-L-A-T-M-C-R-F-G-P-M-I-Q-C-D-L-S-S-D-D). The lunasin polypeptide and the second polypeptide can be covalently linked via disulfide bridges. In some embodiments, the lunasin polypeptide and the second polypeptide are covalently linked by two disulfide bridges.

In some embodiments, a method for purifying lunasin from a plant includes: providing a plant material from the plant; and releasing lunasin from the lunasin-containing complex. In some embodiments, a method for purifying lunasin or a lunasin-containing complex from a plant includes: providing a plant material from the plant; and isolating the lunasin-containing complex from the plant material.

With regard to providing a plant material, in some embodiments, the plant material is any part of the plant containing a lunasin-containing complex. In some embodiments, the plant material is any part of a soybean plant containing a lunasin-containing complex. In some embodiments, the plant material is any soy-based product containing a lunasin-containing complex. In some embodiments, the plant material is a soybean material obtained as a byproduct of soybean processing, such as a byproduct of a process for making soybean oil, e.g., de-fatted soy flour (white flake), processed soy flour, soy germ, etc. In some embodiments, the plant material is a hydrated plant material or an extracted plant material. For example, in some embodiments, the plant material has been hydrated or extracted using water or a buffer such as PBS.

In embodiments wherein the plant material is not hydrated or extracted, the method can further comprise extracting the plant material. The extraction can be conducted, for example, using water or another aqueous solution such as PBS. In some embodiments, the extraction can be conducted for a time sufficient to hydrate the plant material. In some embodiments, the extraction can be conducted for about 2, 3, 4, 5, 6, 7, 8, 9, 10, 11, 12, 13, 14, 15, 16, 17, 18, or more hours.

With regard to releasing lunasin from the lunasin-containing complex, the plant material containing the lunasin complex is contacted with a reducing agent. Any reducing agent can be used. Examples include, but are not limited to: β-mercaptoethanol (BME), dithiothreitol (DTT), tris(2-carboxyethyl)phosphine (TCEP), and 2-aminoethanethiol. As will be recognized by one skilled in the art upon studying this application, the concentration of reducing agent that is used can affect the efficiency with which lunasin is released from the complex.

It will also be recognized that the concentration of the reducing agent that is effective can vary depending, for example, on the particular reducing agent that is selected. A simple study can be conducted to select an effective concentration of the selected reducing agent. For example, with reference to the Examples herein below, samples of plant material can be treated with various concentrations of the selected reducing agent and compared with an untreated control sample to determine a concentration of reducing agent that effectively releases lunasin from the complex.

In some embodiments, BME is used at a concentration of about 100 mM to about 1.5 M (about 0.7% to about 10%). In some embodiments, BME is used at a concentration of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, or a higher concentration.

In some embodiments DTT is used at concentration of about 1 mM to about 2 mM. In some embodiments DTT is used t a concentration of about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.5, 2.4, 2.5 mM, or a higher concentration.

In some embodiments, TCEP is used at a concentration of about 3 mM to about 100 mM. In some embodiments, TCEP is used at a concentration of about 0.1, 0.2, 0.3, 0.4, 0.5, 0.6, 0.7, 0.8, 0.9, 1, 2, 5, 4, 5, 6, 7, 8, 9, 10, 15, 20, 25, 30, 35, 40, 45, 50, 75, 100 mM, or a higher concentration.

Lunasin can be released from the lunasin-containing complex at any step in a purification scheme by using a reducing agent. After the lunasin has been released from the lunasin-containing complex, it can be purified using various methods as described herein, as well as by other methods that may be known or may become known to those skilled in the art.

In some embodiments, the method for purifying lunasin from a plant includes: providing a plant material from the plant; isolating a lunasin-containing complex from the plant material; and releasing lunasin from the lunasin-containing complex. In some embodiments, the lunasin-containing complex is the desired end product, and can be purified and used without treatment with a reducing agent.

Providing the plant material and releasing the lunasin can be conducted as described herein above. With regard to isolating the lunasin-containing complex, in some embodiments, the lunasin complex can be isolated from the plant material before the lunasin is released from the complex. In some embodiments, the lunasin complex can be isolated after the plant material has been hydrated and/or extracted, as described herein above. In some embodiments, the lunasin complex can be isolated by conducting a series of purification steps, or purification and concentration steps. The purification and/or concentration steps can include one or more of the following techniques: ultrafiltration, size-exclusion chromatography, or other size-based filtration techniques; ion-exchange chromatography or other charge-based filtration techniques; and hydrophobic chromatography or other hydrophobicity-based filtration techniques. In some embodiments, the lunasin-containing complex the desired end-product, and it can be purified upon isolation thereof.

In some embodiments, the plant material is extracted in water or another aqueous solution; and the resulting extract is clarified by passage through cheesecloth or Miracloth, or by centrifugation. The clarified extract can be subjected to ultrafiltration and the lunasin complex-containing permeate collected. It is noted that in prior studies involving attempts to purify lunasin from plant material, lower molecular weight membranes have been used and the retentate, not the permeate, has been collected for further processing. This prior strategy is quite distinct from the embodiments of the presently disclosed subject matter in which permeate is collected, because the permeate is often discarded in this type of procedure. In some embodiments, a 50 kD molecular-weight cutoff membrane is used for ultrafiltration and the lunasin complex-containing permeate collected. In some embodiments, a 40 kD molecular-weight cutoff membrane is used for ultrafiltration and the lunasin complex-containing permeate collected. In some embodiments, a 30 kD molecular-weight cutoff membrane is used for ultrafiltration and the lunasin complex-containing permeate collected. In some embodiments, a 20 kD or larger molecular-weight cutoff membrane is used. In some embodiments, a membrane having a molecular-weight cutoff that is larger than about 15 kD is used. In some embodiments, a 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 kD or larger molecular-weight cutoff membrane is used.

In some embodiments, the permeate can then be subjected to ion-exchange chromatography (e.g., quaternary amino (Q) column) to obtain more purified lunasin-containing complex.

In some embodiments, the ion-exchange column-purified lunasin complex can be contacted with a reducing agent, as described herein above.

In some embodiments, the clarified extract can be subjected to ion-exchange chromatography (e.g., Q column) to obtain a partially purified lunasin-containing complex. This partially purified lunasin-containing complex can be subjected to ultrafiltration as described herein above to obtain a more purified lunasin-containing complex.

After the lunasin has been released from the lunasin-containing complex, it can be purified using various methods as described herein, as well as by other methods that may be known or may become known to those skilled in the art. For example, the released lunasin can be subjected purification and/or concentration using techniques such as: ultrafiltration, size-exclusion chromatography, or other size-based filtration techniques; ion-exchange chromatography or other charge-based filtration techniques; hydrophobic chromatography or other hydrophobicity-based filtration techniques such as reverse-phase chromatography; and other protein chromatography methods known to those skilled in the art, to obtain a highly purified lunasin protein.

In some embodiments, after the lunasin is released from the lunasin complex using the reducing agent, it is passed through a butyl hydrophobic chromatography column, and the flow through containing unbound proteins including lunasin is collected. In some embodiments, a concentration step can then be performed. As will be recognized by those skilled in the art, the concentration step can be performed, for example, using a commercially-available membrane-based kits, using a freeze-drying process, or by any other process known to those skilled in the art. In some embodiments, reverse phase chromatography can then be used to obtain a highly-purified lunasin protein. For example, a Source 15RPC column (GE Healthcare Life Sciences) could be used.

As used herein, the terms "purifying," "purify," and "pure," when used in reference to a lunasin-containing complex and/or a lunasin polypeptide refers to a lunasin-containing complex and/or a lunasin polypeptide (or obtaining such) that is substantially free of or includes reduced impurities. In some embodiments, the term(s) refer to at least about 50%, 60%, 70%, 75%, 80%, 85%, 86%, 87%, 88%, 89%, 90%, 91%, 92%, 93%, 94%, 95%, 96%, 97%, 98%, or 99% pure. The term "purified" is used to refer to a pure lunasin-containing complex and/or lunasin polypeptide, as distinguished from a composition that happens to include traces of the lunasin-containing complex and/or lunasin polypeptide.

As used herein, the terms "isolating" or "isolate," when used in reference to a lunasin-containing complex and/or a lunasin polypeptide refers to a separation of a lunasin-containing complex and/or a lunasin polypeptide-containing component of a plant material from other components of a plant material. In this regard, isolating a lunasin-containing complex and/or a lunasin polypeptide can include purifying the lunasin-containing complex and/or the lunasin polypeptide, but is further inclusive of the separation of a lunasin-containing complex and/or a lunasin polypeptide-containing component of a plant material from other components of a plant material, wherein the result is not necessarily a pure lunasin-containing complex and/or a lunasin polypeptide.

It is noted that the steps in the aforementioned embodiments of the method for purifying lunasin from a plant need not be performed in a particular order, and not all of the steps described herein are necessary.

The presently-disclosed subject matter further includes a kit for purifying lunasin or a lunasin-containing complex from a plant. In some embodiments, the kit includes one or more of the following components: instructions for purifying lunasin from a plant; an extraction solution (e.g., water, PBS); a reducing agent; a device useful for purifying and/or concentrating lunasin or a lunasin-containing complex, such as a device useful for performing one of the following techniques: ultrafiltration, size-exclusion chromatography, or other size-based filtration technique; ion-exchange chromatography or other charge-based filtration technique; and hydrophobic chromatography or other hydrophobicity-based filtration technique such as reverse phase chromatography. As will be recognized by those skilled in the art, upon review of the above-described methods for purifying lunasin or a lunasin-containing complex from a plant, additional kit components are apparent and are contemplated for inclusion in a kit in accordance with the presently-disclosed subject matter.

In some embodiments, a composition is provided that includes lunasin as purified in accordance with the presently-disclosed methods. As will be understood by those skilled in the art, formulations of a composition containing the lunasin polypeptide can be provided for various types of delivery, e.g., oral, nasal, topical, injectable, etc. Delivery to mucosal sites, e.g., nasal delivery formulation, has benefits such as increased uptake, and decreased amount of lunasin required for efficacy, because it bypasses digestion, where as much as 95% of orally-administered lunasin can be degraded. The lunasin polypeptide can be formulated as a topical gel/lotion to prevent skin cancer. The lunasin polypeptide can be used as an injectable agent. In some embodiments, the injectable agent can be used as a prophylactic agent in individuals acutely exposed to chemical carcinogens or radiation. It can also be useful as an adjuvant treatment for children undergoing chemo- or radiation-treatment for cancers when there is a concern that the treatments may be mutagenic/carcinogenic.

The presently-disclosed subject matter further includes a lunasin-containing complex comprising a lunasin polypeptide and a second polypeptide. In some embodiments, the lunasin polypeptide comprises the sequence of either SEQ ID NO: 1 (S-K-W-Q-H-Q-Q-D-S-C-R-K-Q-L-Q-G-V-N-L-T-P-C-E-K-H-I-M-E-K-I-Q-G-R-G-D-D-D-D-D-D-D-D) or SEQ ID NO: 2 (S-K-W-Q-H-Q-Q-D-S-C-R-K-Q-L-Q-G-V-N-L-T-P-C-E-K-H-I-M-E-K-I-Q-G-R-G-D-D-D-D-D-D-D-D-N). In some embodiments, the second polypeptide comprises the sequence of SEQ ID NO: 3 (E-G-K-D-E-D-E-E-E-E-G-H-M-Q-K-C-C-T-E-M-S-E-L-R-S-P-K-C-Q-C-K-A-L-Q-K-I-M-E-N-Q-S-E-E-L-E-E-K-Q-K-K-M-E-K-E-L-I-N-L-A-T-M-C-R-F-G-P-M-I-Q-C-D-L-S-S-D-D). The lunasin polypeptide and the second polypeptide can be covalently linked via disulfide bridges. In some embodiments, the lunasin polypeptide and the second polypeptide are covalently linked by two disulfide bridges.

When used herein with reference to the lunasin-containing complex, the term "lunasin polypeptide" is inclusive of wild type lunasin, including wild type lunasin from soybean and other plants, as well as functional variants and functional fragments thereof. For example, the lunasin polypeptide can be a lunasin polypeptide of SEQ ID NO: 1, a lunasin polypeptide of SEQ ID NO: 2, or a lunasin polypeptide as described in U.S. Provisional Patent Application No. 61/254,788 filed on Oct. 26, 2009, which is incorporated herein by this reference. When used herein with reference to the lunasin-containing complex, the term "second polypeptide" is inclusive of the polypeptide comprising SEQ ID NO: 3, as well as functional variants and functional fragments thereof.

The term "fragment", when used in reference to a reference polypeptide, refers to a polypeptide in which amino acid residues are deleted as compared to the reference polypeptide, but where the remaining amino acid sequence is usually identical to the corresponding positions in the reference polypeptide. Such deletions can occur at the amino-terminus or carboxy-terminus of the reference polypeptide, or alternatively both. In some cases, such deletions can occur within the reference polypeptide. Fragments typically are at least 17, 18, 19, 20, 21, 22, 23, 24, 25, 26, 27, 28, 29, 30, 31, 32, 33, 34, 35, 36, 37, 38, 39, 40, 41, or 42 amino acids long.

A fragment can also be a "functional fragment," in which case the fragment retains some or all of the desired activity of the reference polypeptide, or has enhanced activity relative to the reference polypeptide. For example, in some embodiments, a functional fragment of wild type lunasin can retain some or all of the chemotherapeutic activity of the reference polypeptide.

The term "variant" refers to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein, or has enhanced activity relative to the reference polypeptide. For example, a functional variant of a wild type lunasin can retain some or all of the chemotherapeutic activity of the reference polypeptide. The term functional variant does not include variants that lose all chemotherapeutic activity or other desired activity of wild type lunasin.

The term functional variant includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein.

In some embodiments, the complex of the composition can be purified from a plant material, as described herein above. The lunasin-containing complex can be isolated and purified from the plant material, without being treated with a reducing agent to release the lunasin from the complex. In such embodiments, the lunasin polypeptide typically comprises the sequence of either SEQ ID NO: 1 or SEQ ID NO: 2 and the second polypeptide typically comprises the sequence of SEQ ID NO: 3.

As will be recognized by those of ordinary skill in the art, desired embodiments of the lunasin-containing complex can be made using well-known molecular biology techniques.

In some embodiments, the lunasin-containing complex can be used as a nutriceutical additive. In some embodiments, the lunasin-containing complex can be used for treating a cancer. In some embodiments, the lunasin-containing complex can be used for treating an inflammation-related disease.

The presently-disclosed subject matter further includes a kit for purifying the lunasin-containing complex from a plant. In some embodiments, the kit includes one or more of the following components: instructions for purifying the lunasin-containing complex from a plant; an extraction solution (e.g., water, PBS); a device useful for purifying and/or concentrating the lunasin-containing complex, such as a device useful for performing one of the following techniques: ultrafiltration, size-exclusion chromatography, or other size-based filtration technique; ion-exchange chromatography or other charge-based filtration technique; and hydrophobic chromatography or other hydrophobicity-based filtration technique. As will be recognized by those skilled in the art, upon review of the above-described methods for purifying lunasin or a lunasin-containing complex from a plant, additional kit components are apparent and are contemplated for inclusion in a kit in accordance with the presently-disclosed subject matter.

In some embodiments, a composition is provided that includes the lunasin-containing complex as purified in accordance with the presently-disclosed methods or as made using another technique, e.g., well-known molecular biology techniques. As will be understood by those skilled in the art, formulations of composition containing the lunasin-containing complex can be provided for various types of delivery, e.g., oral, nasal, topical, injectable, etc. Delivery to mucosal sites, e.g., nasal delivery formulation, has benefits such as increased uptake, and decreased amount of the lunasin-containing complex required for efficacy, because it bypasses digestion, whereas much as 95% of orally-administered composition can be degraded. The lunasin-containing complex can be formulated as a topical gel/lotion to prevent skin cancer. The lunasin-containing complex can be used as an injectable agent. In some embodiments, the injectable agent can be used as a prophylactic agent in individuals acutely exposed to chemical carcinogens or radiation. It can also be useful as an adjuvant treatment for children undergoing chemo- or radiation-treatment for cancers when there is a concern that the treatments may be mutagenic/carcinogenic.

The presently-disclosed subject matter further includes a kit including a lunasin containing complex, for example, contained in a vial or vessel. In some embodiments, the kit can further include instructions for treatment of a condition of interest using the lunasin-containing complex. In some embodiments, the kit can include means for administering the lunasin-containing complex. As will be recognized by those skilled in the art upon review of this application, means for administration will be apparent depending on the desired mode of administration. For example, for administration by injection, a syringe could be included. For other examples, for topical administration, a patch could be included; for oral administration, a consumable liquid or container appropriate for holding a consumable liquid could be included to aide the oral administration; for nasal delivery, a nasal spray device or cotton swab could be included to aide the nasal-administration; etc.

The presently-disclosed subject matter further includes a method for treating a cancer and/or treating an inflammation-related disease using lunasin as purified by the methods described herein, or a composition comprising lunasin and/or a lunasin-containing complex. In some embodiments, the method includes administering the composition comprising the lunasin polypeptide and/or a lunasin-containing complex, as described herein, to a subject in need thereof.

In some embodiments, a composition is provided that includes: (a) a lunasin polypeptide and/or a lunasin-containing complex, as purified in accordance with the presently-disclosed methods or as made using another technique, e.g., well-known molecular biology techniques; and (b) curcumin (also known as (1E, 6E)-1,7-bis (4-hydroxy-3-methoxyphenyl)-1,6-heptadiene-3,5-dione; diferuloylmethane, natural yellow 3, and by other names). The combination of the lunasin polypeptide or lunasin-containing complex and the curcumin has a synergistic effect, for example, a synergistic effect on the treatment of a cancer or an inflammation-related disease, e.g., a synergistic antiproliferative effect on cancer cells.

As used herein, "synergy" and "synergistic effect" can refer to any substantial enhancement, in a composition of at least two compounds, of a measurable effect, e.g., an anti-cancer effect, when compared with the effect of a component of the composition, e.g., one active compound alone, or the complete blend of compounds minus at least one compound. Synergy is a specific feature of a blend of compounds, and is above any background level of enhancement that would be due solely to, e.g., additive effects of any random combination of ingredients.

As will be understood by those skilled in the art, formulations of a composition containing the lunasin polypeptide and/or lunasin-containing complex and curcumin can be provided for various types of delivery, e.g., oral, nasal, topical, injectable, etc. Delivery to mucosal sites, e.g., nasal delivery formulation, has benefits such as increased uptake, and decreased amount of the lunasin-containing complex required for efficacy, because it bypasses digestion, where as much as 95% of orally-administered composition can be degraded. The composition can be formulated as a topical gel/lotion to prevent skin cancer. The composition can be used as an injectable agent. In some embodiments, the injectable agent can be used as a prophylactic agent in individuals acutely exposed to chemical carcinogens or radiation. It can also be useful as an adjuvant treatment for children undergoing chemo- or radiation-treatment for cancers when there is a concern that the treatments may be mutagenic/carcinogenic.

The presently-disclosed subject matter further includes a kit including a lunasin polypeptide and/or lunasin containing complex and curcumin, for example, contained in one or more vials or vessels. In some embodiments, the kit can include a vial containing a purified lunasin polypeptide or lunasin-containing complex, and curcumin; or packaged together, a first vial containing a purified lunasin polypeptide or lunasin-containing complex, and a second vial containing curcumin. In some embodiments, the kit can further include instructions for treatment of a condition of interest using the composition. In some embodiments, the kit can include means for administering the composition. As will be recognized by those skilled in the art upon review of this application, means for administration will be apparent depending on the desired mode of administration. For example, for administration by injection, a syringe could be included. For other examples, for topical administration, a patch could be included; for oral administration, a consumable liquid or container appropriate for holding a consumable liquid could be included to aide the oral administration; for nasal delivery, a nasal spray device or cotton swab could be included to aide the nasal administration; etc.

The presently-disclosed subject matter further includes a method for treating a cancer and/or treating an inflammation-related disease using a composition including a lunasin polypeptide and/or a lunasin-containing complex; and curcumin, wherein the combination of the a lunasin polypeptide or lunasin-containing complex and the curcumin has a synergistic effect. In some embodiments, the method includes administering the composition to a subject in need thereof. The term "cancer" refers to all types of cancer or neoplasm or malignant tumors found in animals, including leukemias, carcinomas, melanomas, and sarcomas. Examples of cancers include cancers of the brain, bladder, breast, cervix, colon, head and neck, kidney, lung, non-small cell lung, mesothelioma, ovary, prostate, sarcoma, stomach, uterus and Medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocyte system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, pre-malignant skin lesions, testicular cancer, thyroid cancer, neuroblastoma, esophageal cancer, genitourinary tract cancer, malignant hypercalcemia, cervical cancer, endometrial cancer, and adrenal cortical cancer.

As used herein, the term, "inflammation-related disease" includes diseases or disorders which are caused, at least in part, or exacerbated, by inflammation, which is generally characterized by increased blood flow, edema, activation of immune cells, (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cancer, or other agents.

Inflammation-related diseases include acute inflammation-related diseases, chronic inflammation-related diseases, and recurrent inflammation-related diseases. Acute inflammation-related diseases, are generally of relatively short duration, and last for from about a few minutes to about one to two days, although they can last several weeks. Characteristics of acute inflammation-related diseases include increased blood flow, exudation of fluid and plasma proteins (edema) and emigration of leukocytes, such as neutrophils. Chronic inflammation-related diseases, generally, are of longer duration, e.g., weeks to months to years or longer, and are associated histologically with the presence of lymphocytes and macrophages and with proliferation of blood vessels and connective tissue. Recurrent inflammation-related diseases include disorders which recur after a period of time or which have periodic episodes. Some inflammation-related diseases fall within one or more categories. Inflammation-related diseases may additionally include, but are not limited to, diseases and disorders such as artherosclerosis, arthritis, inflammation-promoted cancers, asthma, autoimmune uveitis, adoptive immune response, dermatitis, multiple sclerosis, diabetic complications, and inflammatory bowel disease.

As used herein, the terms "treatment" or "treating" relate to any treatment of a condition of interest (e.g., cancer and/or an inflammation-related disease), including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

As used herein, the term "subject" refers to human and other animal subjects. Thus, veterinary therapeutic uses are provided in accordance with the presently disclosed subject matter. For example, a prophylactic treatment is contemplated for animals that have a genetic susceptibility to developing specific cancers.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine; including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided for is the treatment of livestock, including, but not limited to, domesticated swine, ruminants, ungulates, horses (including race horses), poultry, and the like.

The presently-disclosed subject matter is further illustrated by the following specific but non-limiting examples. The following examples may include compilations of data that are representative of data gathered at various times during the course of development and experimentation related to the present invention.

Examples

Soybean plant material was provided, extracted using PBS, filtered using a 50 kD MWCO membrane, and the collected permeate was subjected to ion-exchange chromatography using a quaternary amino (Q) column to obtain a protein-containing fraction identified in these examples as the "Q-pool."

FIG. 1 includes the results of an analysis of the purified lunasin-containing complex using non-reducing and reducing sodium dodecyl sulfate (SDS) polyacrylamide gel electrophoresis (PAGE). The lunasin-containing complex was purified from soybean white flake using a combination of extraction, clarification, anion-exchange chromatography and ultrafiltration. Aliquots of the purified lunasin-containing complex were subjected to SDS PAGE in the presence or absence of the reducing agent beta-mercaptoethanol (BME). Panel A includes a coomassie-stained SDS-PAGE gel and Panel B includes a corresponding immunoblot probed with an antibody specific for lunasin. Lanes 1 and 2 represent lunasin (5.1 kDa) and lunasin-containing complex (14.1 kDa) respectively under non-reducing conditions while lanes 3 and 4 represent the same under reducing conditions in the presence of BME. Lane 4 shows that BME results in the release of free lunasin (5.1 kDa) from the complex.

With reference to FIG. 1, aliquots of the Q-pool were analyzed by SDS-PAGE, deviating from typical SDS-PAGE sample preparation protocol in that one aliquot was not subjected to treatment with any reducing agent, and the other aliquots were subjected to pre-treatment with the reducing agent, β-mercaptoethanol (BME). As illustrated in FIG. 1, treatment with BME released lunasin from the complex, demonstrating that lunasin can be released from the complex by reducing disulfide bonds.

Figure 2:
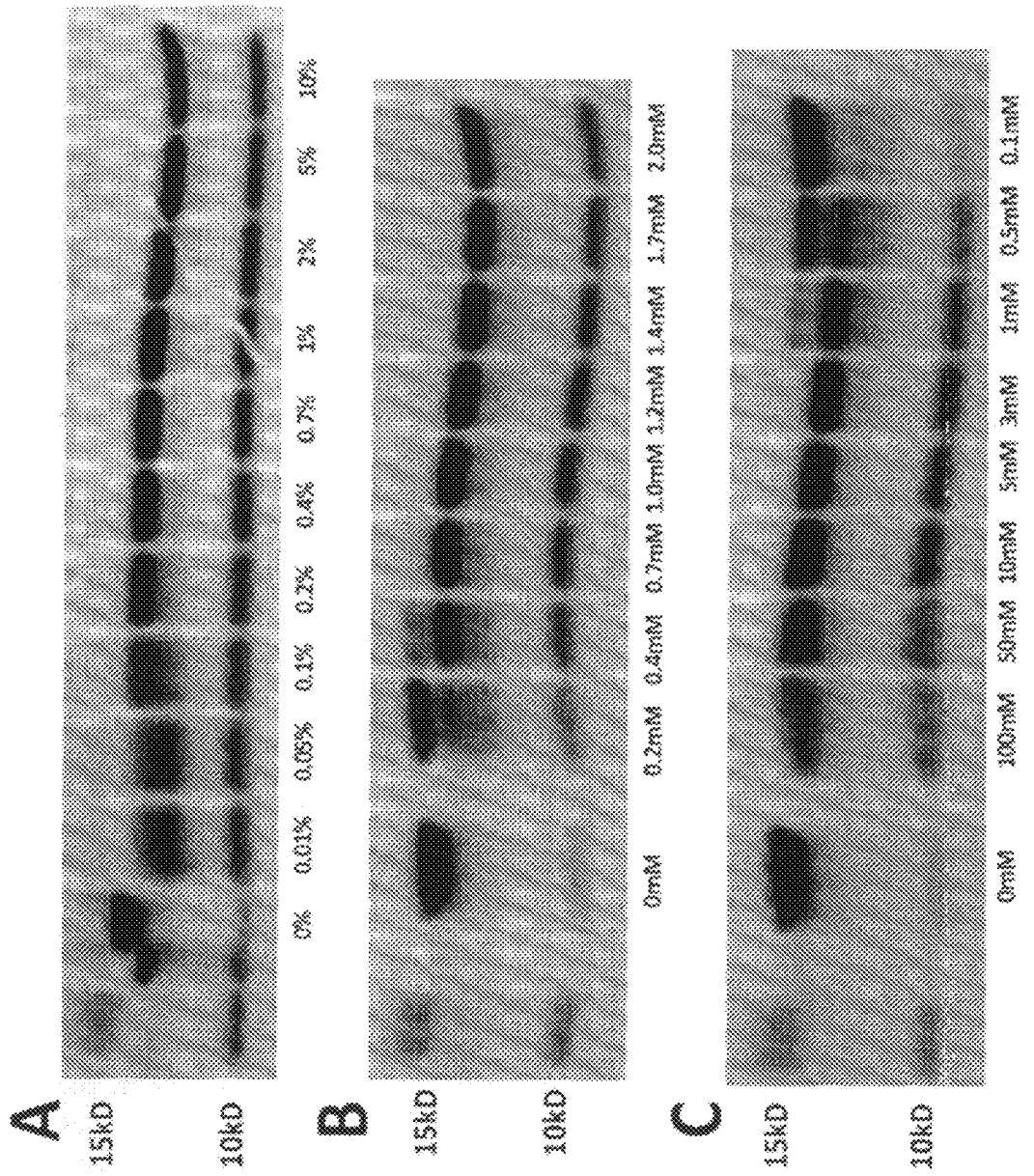
FIG. 2 is an image of an SDS-PAGE gel where a purified lunasin-containing complex was subjected to various concentrations of the reducing agents beta-mercaptoethanol (BME), dithiothreitol (DTT), and tris(2-carboxyethyl)phosphine (TCEP).

The use of reducing agents to release lunasin from a lunasin-containing complex was studied. Lunasin-containing complex was purified from soybean white flake using a combination of extraction, clarification, anion-exchange chromatography and ultrafiltration. With reference to FIG. 2, aliquots of a Q-pool were obtained as described above, and were analyzed by SDS-PAGE. One aliquot was not subjected to treatment with any reducing agent, and the other aliquots were subjected to pre-treatment with BME in various concentrations ranging from 0.01% BME to 10% BME. Aliquots of the purified lunasin-containing complex were treated with various concentrations of the reducing agents: (Panel A) beta-mercaptoethanol (BME), (Panel B) dithiothreitol (DTT), and (Panel C) tris(2-carboxyethyl)phosphine (TCEP) for 1 hour at room temperature. Treated samples were added to sample loading buffer without BME and then subjected to SDS PAGE and the proteins stained with coomasie.

As illustrated in FIG. 2, Panel A, even low concentrations (e.g., about 0.7% or 100 mM) of BME released lunasin from the lunasin-containing complex contained in the Q-pool. Similarly, other aliquots of the Q-pool were treated with the reducing agent, dithiothreitol (DTT), in various concentrations ranging from 0.2 mM DTT to 2.0 mM DTT. As illustrated in FIG. 2, Panel B, treatment with even low concentrations (e.g., about 1 mM) of DTT released lunasin from the lunasin-containing complex contained in the Q-pool. Similarly, aliquots of a Q-pool were obtained as described above in this example were subjected to pre-treatment with the reducing agent, tris(2-carboxyethyl)phosphine (TCEP), in various concentrations ranging from 2.0 mM TCEP to 100 mM TCEP. As illustrated in FIG. 2, Panel C, treatment with even low concentrations (e.g., about 3 mM) of TCEP released lunasin from the lunasin-containing complex contained in the Q-pool. The results demonstrate that the lunasin present in the lunasin-containing complex can be efficiently released by treating with a variety of reducing agents. Specific conditions that were found to be useful in the analysis include BME; 0.7%-10% (100 mM-1.43 M), DTT: 1 mM-2 mM, and TCEP: 3 mM-100 mM.

The ability of lunasin, purified from soybean white flake in accordance with the presently-disclosed subject matter, to bind the cores histones H3 and H4 was studied. Previous studies suggest that one of the biological activities of lunasin is to bind deacetylated core histones H3 and H4. To confirm the biological activity of the lunasin purified from soybean white flake using the methods in the subject matter disclosed herein, an in vitro binding assay was used to assess binding to the human H3 and H4 proteins.

Increasing amounts of histone 3.3 (hH3.3) and histone 4 (hH4) were bound to wells of a 9.6-well microtiter plate. Different amounts of either synthetic lunasin or purified lunasin were added to the wells and allowed to bind. The concentration of lunasin bound was determined using a polyclonal antibody against lunasin and a horseradish peroxidase conjugated antibody that recognizes the lunasin antibody. Binding was quantitated by measuring the absorbance at 450 nm.

Figure 3:
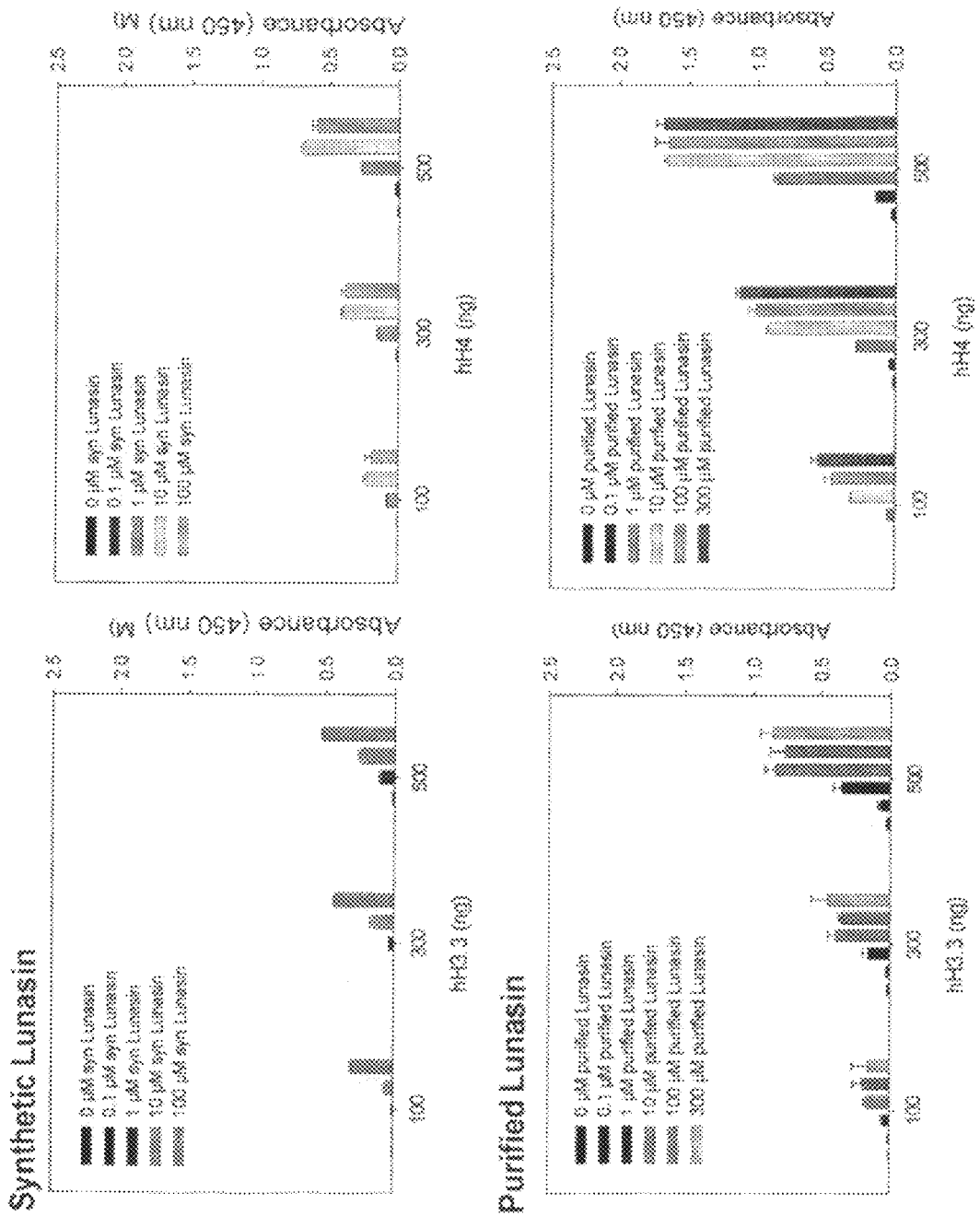
FIG. 3 compares the ability of soybean-derived lunasin and a synthetic lunasin to bind to the human core histones H3 and H4 in vitro.

With reference to FIG. 3, highly purified soybean-derived lunasin was used in an in vitro histone binding assay to assess this previously reported biological activity, as described above. As illustrated in FIG. 3, the soybean-derived lunasin specifically binds human histones H3 and H4 with an affinity greater than that observed using a synthetic lunasin created by peptide synthesis.

Soybean-derived lunasin bound to both H4 and H3 in a dose dependent manner, with lunasin exhibiting a higher affinity for H4 than for H3. Similarly, synthetic lunasin exhibited more binding to H4 compared to H3, however the binding was lower than observed using the soybean-derived lunasin. These results show that lunasin preferentially binds to H4 over H3 and that the lunasin purified from soybean is biologically active and binds histones more effectively than synthetic lunasin comprised of SEQ ID NO: 1.

The ability of lunasin, purified from soybean white flake in accordance with the presently-disclosed subject matter, to inhibit the proliferation of specific cancer cell lines was studied. Recent studies have shown that lunasin and lunasin-containing protein preparations can inhibit the proliferation of several cancer cell lines in vitro. To further assess and confirm the biological activity of lunasin and the lunasin-containing complex, cell proliferation assays were conducted with a panel of established cancer cell lines.

A panel of cancer cell lines was collected from colleagues or purchased from the American Type Culture Collection. Cells were grown in the appropriate medium and treated with PBS (control), lunasin (30 or 100 µM), or the lunasin-containing complex (10 or 30 µM) for 72 hours. Cell viability was assessed using a standard [3-(4,5-dimethylthiazol-2-yl)-5-(3-carboxymethoxy-phenyl)-2-(4-sulfo-phenyl)-2H-tetrazolium (MTS) assay. The data shown (FIG. 4) represent the number of viable cells relative to the PBS-treated controls. The human cell lines tested were: H661, non-small cell lung cancer; H1299, non-small cell lung cancer; SKBR3, adenocarcinoma mammary gland origin; MDA-MB-231, adenocarcinoma, mammary gland origin; MCF-7, adenocarcinoma, mammary gland origin; and HT-29, adenocarcinoma, colon origin.

Figure 4:
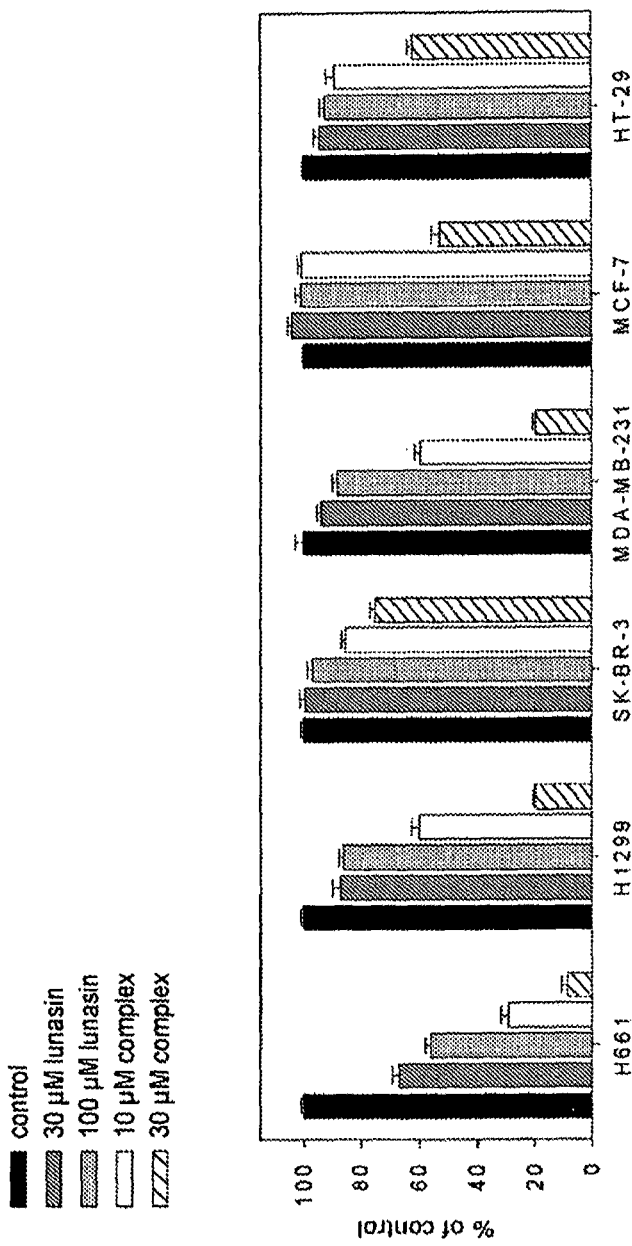
FIG. 4 demonstrates the ability of soybean-derived lunasin and the lunasin-containing complex to inhibit the growth of specific cancer cell lines.

With reference to FIG. 4, highly purified soybean-derived lunasin was used in an in vitro cell proliferation assays to assess the activity of lunasin against specific cancer cell lines. As illustrated in FIG. 4, the soybean-derived lunasin exhibited the ability to significantly inhibit the growth of H661 cells, with a minor effect on H1299 and MDA-MB-231 cells over a 3 day period. However, all cell lines tested thus far have exhibited reduced proliferation when treated with the lunasin-containing complex, with the H661, H1299, and MDA-MB-231 cells being the most sensitive.

The soybean-derived lunasin exhibited the ability to significantly inhibit the growth of H661 cells, with a minor effect on H1299 and MDA-MB-231 cells over a 3 day period. However, all cell lines tested thus far have exhibited reduced proliferation when treated with the lunasin-containing complex, with the H661, H1299, and MDA-MB-231 cells being the most sensitive. These results reinforce previous observations that lunasin's antiproliferative activity against cancer is cell-line specific and indicate that the lunasin-containing complex is more effective than the lunasin peptide alone. These results also expand the number of cancer types that may be sensitive to lunasin-based therapies.

The following MS methods were used in studies described herein.

ESI-MS Analysis of Lunasin Complex: Purified lunasin complex was desalted with 18 ZipTip (Millipore, Billerica, Mass.) and ESI spectra of lunasin complex was obtained by Orbitrap XL mass spectrometer (Thermo Scientific, San Jose, Calif.) equipped with TriVersa NanoMate system (Advion Biosciences, Ithaca, N.Y.). The MS spectra were deconvoluted with Xtract (Thermo Scientific, San Jose, Calif.). To analyze subunits of lunasin complex, purified lunasin complex was reduced with 5 mM dithiothreitol (DTT) at 70° C. for 15 minutes, followed by alkylation with 15 mM iodoacetamide (IAA) at room temperature in the dark for 15 min. Reduced lunasin complex samples, with or without further alkylation, were desalted with C18 ZipTip and analyzed by Orbitrap XL.

LC/MS/MS Analysis of Lunasin Subunits: Purified lunasin subunits were desalted with PepClean C18 spin column (Pierce, Rockford, Ill.), reduced with DTT, alkylated with IAA, and incubated with sequencing grade modified trypsin (Promega, Madison, Wis.) at 37° C. overnight. Incubation was stopped by adding 5% formic acid to the samples and the digests were loaded on to a Hypersil Gold C18 column and separated by Accela HPLC system (Thermo Scientific, San Jose, Calif.) with an acetonitrile and 0.1% formic acid gradient. The eluted peptides were directed to Orbitrap XL mass spectrometer and MS/MS spectra of the peptides were acquired in data dependent scan mode.

Figure 5:
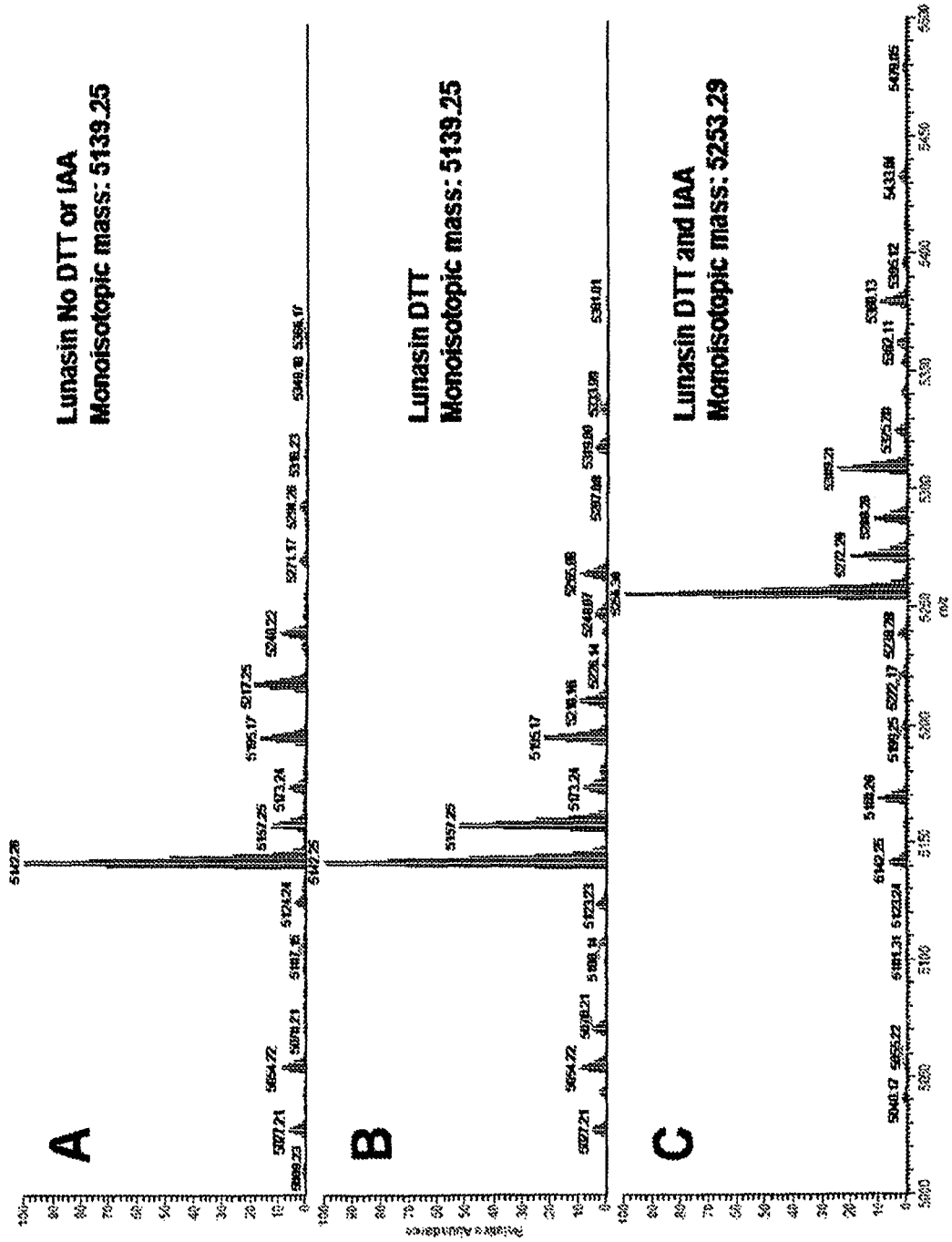
FIG. 5 includes mass spectra obtained after deconvolution for samples comprised of the purified soybean-derived lunasin that demonstrates this peptide has the amino acid sequence defined by SEQ ID NO: 2.

With reference to FIG. 5, mass spectra were obtained after deconvolution for samples of the highly purified soybean-derived lunasin. Purified soybean-derived lunasin, obtained in accordance with the presently-disclosed subject matter, was desalted using a C18 spin column and analyzed before (FIG. 5, Panel A) and after treatment with DTT alone (FIG. 5, Panel B) or a combination of DTT and IAA (iodoacetamide, FIG. 5, Panel C). MS spectra of the untreated sample indicated that the protein has no disulfide bond and two Cys residues. The monoisotopic mass of the protein is 5139.25, which is 114.02 Da higher than the expected monoisotopic mass of the published form of lunasin (5025.23, small peak in the spectrum). The mass difference indicates that there might be an additional Asn residue in the soybean-derived lunasin. Additional peaks of combinations of +16 (Met oxidation), +22 (Na), and +38 (K) were also detected.

A sample treated with DTT and IAA was digested with trypsin and analyzed by LC/MS/MS. Several peptides from lunasin were detected. That confirmed that the protein is related to lunasin but it did not distinguish whether there is an additional Asn residue. According to soybean albumin precursor sequence, the additional Asn is likely at the C-terminus of lunasin. LC/MS data was examined to identify the C-terminus of the protein. C-terminus of lunasin (GD$_9$, m/z 1111.28) was not found, instead a weak peak of m/z 1225.32 (matches with G D$_9$N) was found. LC/MS/MS experiment was set to specifically acquire MS/MS spectrum of the m/z 1225.32 peak. The MS/MS spectrum of m/z 1225.32 matched perfectly with G D$_9$N (Slide #4), which confirmed that there is an additional Asn at C-terminus of the protein.

The data shown in FIG. 5 illustrate that the native molecular weight of this lunasin is 5139.25 m/z, which corresponds to a lunasin polypeptide of SEQ ID NO: 2. These results suggest that previously-reported studies have not identified the predominant form of lunasin present in soybean, and perhaps other plants.

Figure 6:
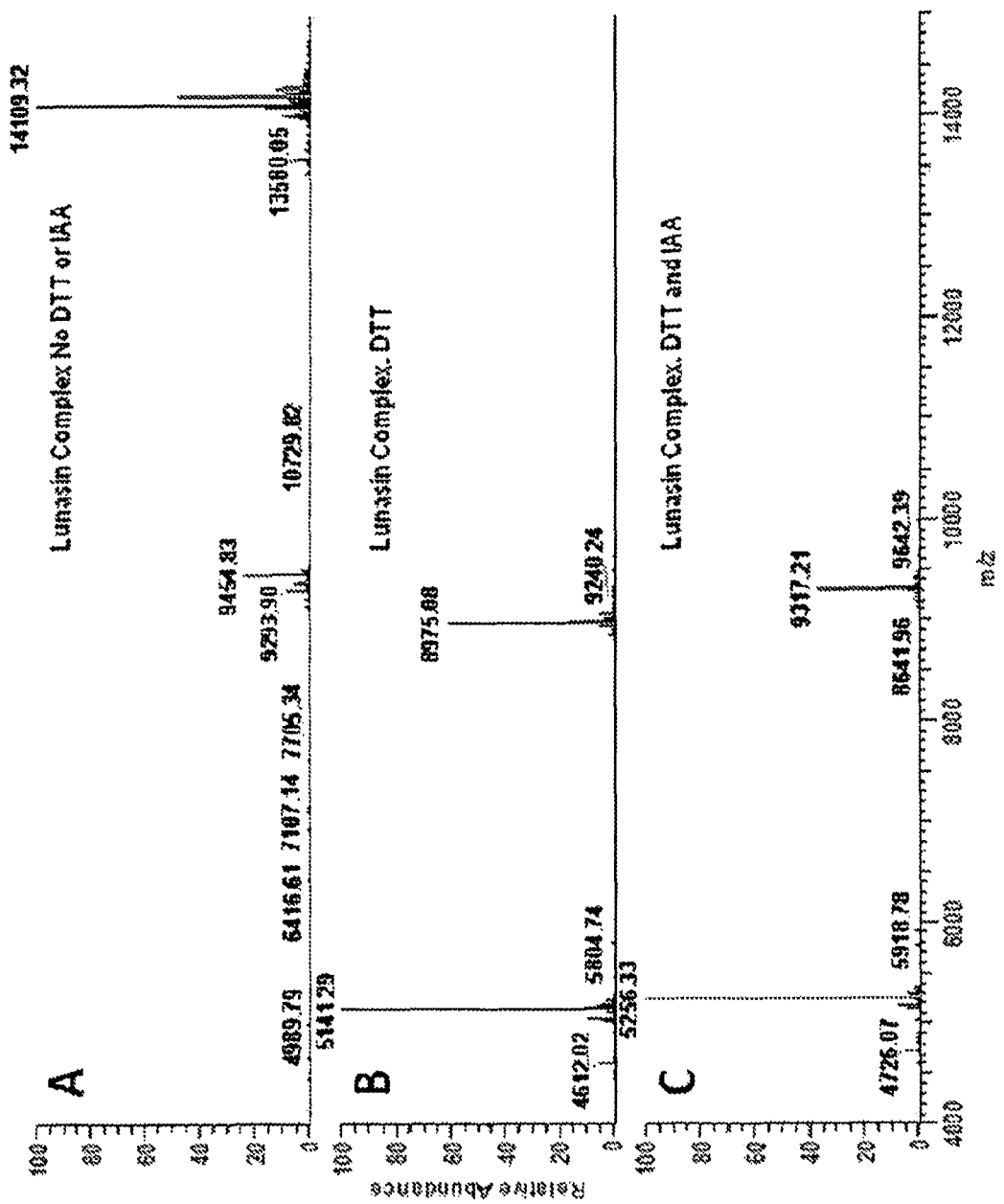
FIG. 6 includes mass spectra obtained after deconvolution for samples including the lunasin-containing complex that identify the peptides in the complex as those defined by SEQ ID NO: 2 and SEQ ID NO: 3.

With reference to FIG. 6, mass spectra were obtained after deconvolution for samples including the lunasin-containing complex. Panel A: Spectrum of purified lunasin complex (most abundant isotopic peak at 14109.3 Da). The peak adjacent to lunasin complex (14207.3 Da) is the adduct peak of lunasin complex with phosphoric acid (plus 98 Da). Panel B: Spectrum of reduced lunasin complex. The most abundant isotopic peaks shown in the spectrum are lunasin (5141.3 Da) and soybean albumin long chain (8975.1 Da). Panel C: Spectrum of lunasin complex treated with DTT and IAA. The most abundant peaks shown in the spectrum are lunasin (5256.3 Da) and soybean albumin long chain (9317.2 Da). The monoisotopic peaks are 5139.28 Da and 5253.33 Da for lunasin and lunasin treated with DTT and IAA respectively. The monoisotopic peaks of lunasin complex and soybean albumin long chain were too low to be detected.

Since alkylation of each cysteine by IAA will increase mass by 57 Da, mass shifts of the subunits (Panel C in FIG. X) caused by alkylation of reduced subunits indicated that there are 2 cysteine residues in lunasin (monoisotopic mass increased by 114 Da after alkylation) and 6 cysteine residues in soybean albumin long chain (most abundant mass increased by 342.1 Da after alkylation).

The data of FIG. 6 show that the native molecular weight of the non-reduced lunasin-containing complex included in the samples is 14,109 m/z, which corresponds to a lunasin polypeptide of SEQ ID NO: 2 in complex with a second polypeptide of SEQ ID NO: 3. The data included in the last panel of FIG. 6 indicates the number of cysteine residues. Without wishing to be bound by theory or mechanism, the present inventors' current analysis indicates that the lunasin-containing complex is formed by two disulfide bridges, involving both of the cysteine residues of the lunasin polypeptide and two of the six cysteine residues of the second polypeptide.

Figure 7:
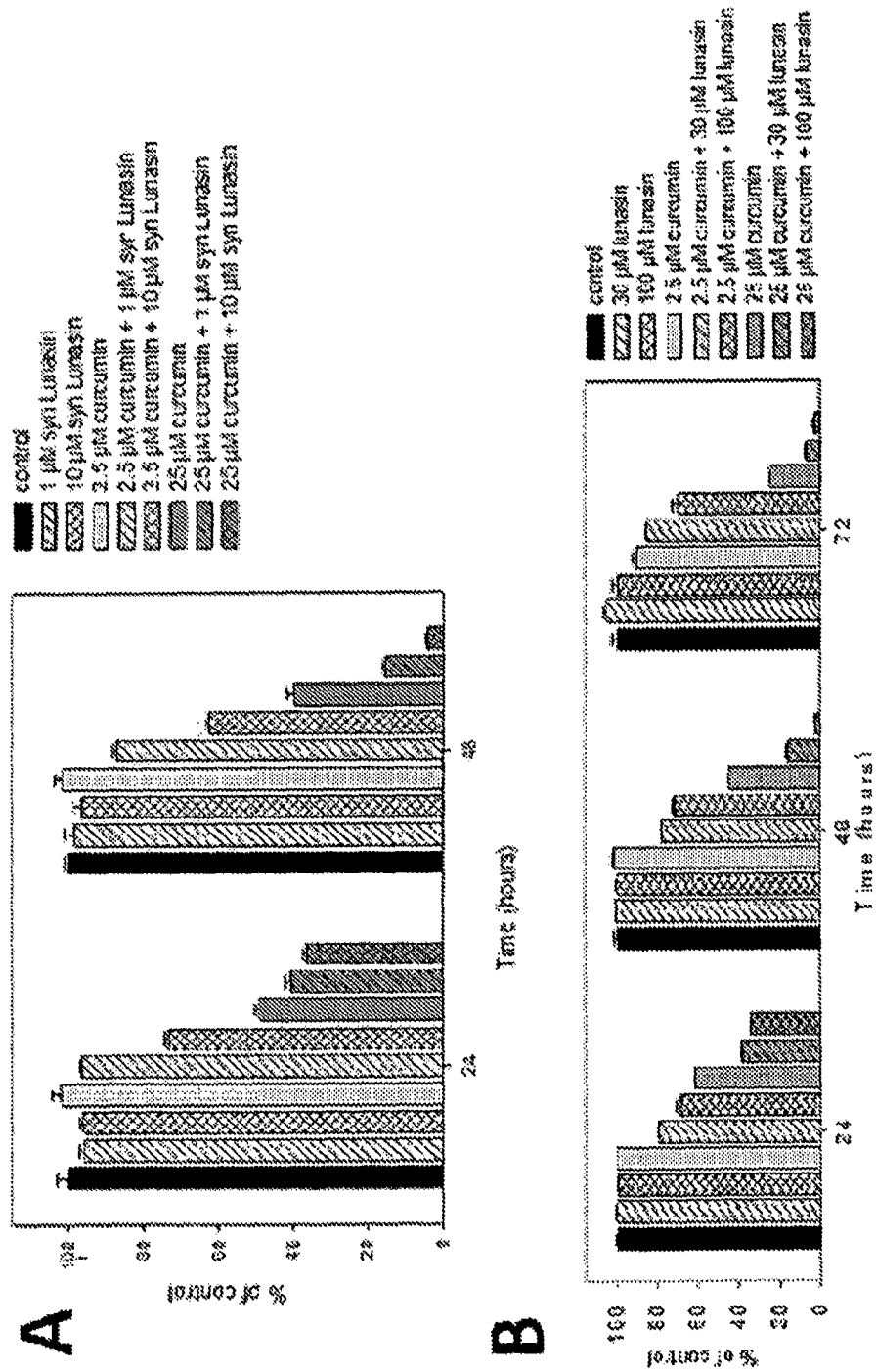
FIGS. 7A and 7B include the results of MTS cell proliferation assays, using SK-BR-3 human breast cancer cells, performed in the absence or presence of either synthetic lunasin or purified soybean-derived lunasin in combination with curcumin over a 1-3 day period.

Turning now to FIG. 7, a synergistic antiproliferative effect of lunasin in combination with curcumin was surprisingly and unexpectedly discovered. MTS cell proliferation assays using SK-BR-3 human breast cancer cells were performed in the absence or presence of either synthetic lunasin or purified soybean-derived lunasin in combination with curcumin over a 2-3 day period. SK-BR-3 cells, whose growth were unaffected by lunasin alone, were inhibited up to 98% when combined with curcumin.

With reference to FIG. 7, synthetic lunasin and highly purified soybean-derived lunasin were used in combination with curcumin in an in vitro cell proliferation assays to assess the activity of lunasin against specific cancer cell lines. As illustrated in FIG. 7, both the synthetic lunasin polypeptide corresponding to SEQ ID NO: 1 and the highly purified lunasin polypeptide corresponding to SEQ ID NO: 2 significantly enhanced the antiproliferative effect of curcumin SK-RB-3 breast cancer cells. These results indicate that combination therapies utilizing a combination of lunasin and curcumin, are more effective in inhibiting cancer cell growth compared to the either treatment alone.

Throughout this document, various references are mentioned. All such references are incorporated herein by reference, including the references set forth in the following list:

REFERENCES

1. Ampe, C., VanDamme, J., deCastro, L. A. B., Sampaio, M. J. A. M., VanMontagu, M., Vandekerckhove, J. (1986). The amino-acid sequence of the 2S sulphur-rich proteins from seeds of Brazil nut (*Bertholletia excelsa* H.B.K.). *Eur. J. Biochem.* 159:597-604.
2. Balasubramanyam, K. et al. (2004). Curcumin, a novel p300/CREB-binding protein-specific inhibitor of acetyltransferase, represses the acetylation of histone/nonhistone proteins and histone acetyltransferase-dependent chromatin transcription. *J Biol Chem.* 279(49):51163-71.
3. Chiesa, G., Rigamonti, E., Lovati, M. R., Disconzi, E., Soldati, S., Sacco, M. G., Cato, E. M., Patton, V., Scanziani, E., Vezzoni, P., Arnoldi, A., Locati, D., and Sirtori, C. R. (2008). Reduced mammary tumor progression in a transgenic mouse model fed an isoflavone-poor soy protein concentrate. *Mol Nutr Food Res.* 52(10):1121-9.
4. de Lumen, B. O. (2008). Lunasin: a novel cancer preventive seed peptide that modifies chromatin. *J AOAC Int.* 91(4): 932-935.
5. de Lumen, B. O. (2005). Lunasin: a cancer-preventive soy peptide. Nutr Rev. 63(1):16-21.
6. de Mejia, E. G., Wang, W., and Dia, V. P. (2010). Lunasin, with an arginine-glycine-aspartic acid motif, causes apoptosis to L1210 leukemia cells by activation of caspase-3. *Mol Nutr Food Res.* 54(3):406-414.
7. de Mejia, E. G., and Dia, V. P. (2009). Lunasin and lunasin-like peptides inhibit inflammation through suppression of NF-kappaB pathway in the macrophage. *Peptides* 30(12): 2388-2398.
8. de Mejia, E. and de Lumen, B. (2006). Soybean bioactive peptides: A new horizon in preventing chronic diseases. *Sexuality Reproduction and Menopause.* 4(2):91-95.
9. de Mejia, E. G., Bradford, T., and Hasler, C. (2003). The anticarcinogenic potential of soybean lectin and lunasin. *Nutr Rev.* 61 (7):239-246.
10. Dia, V. P., and Mejia, E. G. (2010). Lunasin promotes apoptosis in human colon cancer cells by mitochondrial pathway activation and induction of nuclear clusterin expression. *Cancer Lett.* 295(1):44-53.
11. Dia, V. P., Wang, W., Oh, V. L., de Lumen, B. O., and de Mejia, E. G. (2009). Isolation, purification and characterization of lunasin from defatted soybean flour and in vitro evaluation of its anti-inflammatory activity. *Food Chemistry* 114:108-115.
12. Dia, V. P., Torres, S., De Lumen, B. O., Erdman, J. W., Jr., and De Mejia, E. G. (2009). Presence of lunasin in plasma of men after soy protein consumption. *J Agric Food Chem.* 57(4):1260-1266.
13. Dia, V. P., Berhow, M. A., and Gonzalez de Mejia, E. (2008). Bowman-Birk inhibitor and genistein among soy compounds that synergistically inhibit nitric oxide and prostaglandin E2 pathways in lipopolysaccharide-induced macrophages. *J Agric Food Chem.* 56(24):1707-11717.
14. Elayadi, A N., et a). (2007). A peptide selected by biopanning identifies the integrin alphavbeta6 as a prognostic biomarker for nonsmall cell lung cancer. *Cancer Res.* 67(12):5889-95.
15. Ericson, M. L.; Rodin, J., Lenman, M., Glimelius, K., Josefsson, L-G, Rask, L. (1986) Structure of the Rapeseed 1.7 S Storage Protein, Napin, and its Precursor. *J. Biological Chem.* 261:14576-14581.
16. Fullwood, M. J. and Ruan, Y. (2009). ChIP-based methods for the identification of long-range chromatin interactions. *J Cell Biochem.* 107(1):30-9.
17. Galvez, A. F., Chen, N., Macasieb, J., and de Lumen, B. O. (2001). Chemopreventive property of a soybean peptide (lunasin) that binds to deacetylated histones and inhibits acetylation. *Cancer Res.* 61:7473-7478.
18. Galvez, A. F., and de Lumen, B. O. (1999). A soybean cDNA encoding a chromatin-binding peptide inhibits mitosis of mammalian cells. *Nat Biotechnol.* 17(5):495-500.
19. Go, V. L., Wong, D. A. and Butrum, R. (2001) Diet, nutrition and cancer prevention: where are we going from here? *J Nutr.* 131(11 Suppl):3121S-6S.
20. Gonzales de Mejia, E., Vasconez, M., de Lumen, B. O. and Nelson, R. (2004). Lunasin concentration in different soybean genotypes, commercial soy protein, and isoflavone products. *J Agric Food Chem.* 52(19).5882-5887.
21. Hernandez-Ledesma, B., Hsieh, C. C., and de Lumen, B. O. (2009). Antioxidant and anti-inflammatory properties of cancer preventive peptide lunasin in RAW 264.7 macrophages. *Biochem Biophys Res Commun.* 390(3):803-8.
22. Hernandez-Ledesma, B., Hsieh, C. C., and de Lumen, B. O. (2009). Lunasin, a novel seed peptide for cancer prevention. *Peptides* 30(2)426-430.
23. Hernandez-Ledesma, B., and de Lumen, B. O. (2008) Lunasin, a novel cancer preventive peptide. *Perspect Medicin Chem.* 2:75-80.
24. Hsieh, C. C., Hernandez-Ledesma, B., Jeong, H. J., Park, J. H., and de Lumen, B. O. (2010b). Complementary roles in cancer prevention: protease inhibitor makes the cancer preventive peptide lunasin bioavailable. *PLoS One.* 5(1): e8890.
25. Hsieh, C. C., Hernandez-Ledesma, B., and de Lumen, B. O. (2010a). Lunasin, a novel seed peptide, sensitizes human breast cancer MDA-MB-231 cells to aspirin-arrested cell cycle and induced apoptosis. *Chem Biol Interact.* 186(2):127-134.
26. Hsieh, E. A., Chai, C. M., de Lumen, B. O., Neese, R. A., and Hellerstein, M. K. (2004). Dynamics of keratinocytes in vivo using HO labeling: a sensitive marker of epidermal proliferation state. *J Invest Dermatol.* 123(3):530-536.
27. Hu, J., Wang, Y., and Chen, Y. (2009). Curcumin-induced histone acetylation in malignant hematologic cells. *J Huazhong Univ Sci Technolog Med Sci.* 29(1):25-28.
28. Jeong, J. B., deLumen, B. O., and Jeong, H. J. (2010). Lunasin peptide purified from *Solanum nigrum* L. protects DNA from oxidative damage by suppressing the generation of hydroxyl radical via blocking fenton reaction. *Cancer Lett.*
29. Jeong, H. J., Lee, J. R., Jeong, J. B., Park, J. H., Cheong, Y. K., and de Lumen, B. O. (2009). The cancer preventive seed peptide lunasin from rye is bioavailable and bioactive. *Nutr Cancer* 61(5)680-686.
30. Jeong, J. B., Jeong, H. J., Park, J. H., Lee, S. H., Lee, J. R., Lee, H. K., Chung, G. Y., Choi, J. D., and de Lumen, B. O. (2007c). Cancer-preventive peptide lunasin from *Solanum nigrum* L. inhibits acetylation of core histones H3 and H4 and phosphorylation of retinoblastoma protein (Rb). *J Agric Food Chem.* 55(26)10707-10713.
31. Jeong, H. J., Jeong, J. B., Kim, D. S., Park, J. H., Lee, J. B., Kweon, D. H, Chung, G. Y., Seo, E. W., and de Lumen, B. O. (2007b). The cancer preventive peptide lunasin from wheat inhibits core histone acetylation. *Cancer Lett.* 255: 42-48.
32. Jeong, H. J., Jeong, J. B., Kim, D. S., and de Lumen, B. O. (2007a). Inhibition of core histone acetylation by the cancer preventive peptide lunasin. *J Agric Food Chem.* 5:632-637.
33. Jeong, H. J., Park, J. H., Lam, Y., and de Lumen, B. O. (2003). Characterization of lunasin isolated from soybean. *J Agric Food Chem.* 51(27):7901-7906.
34. Jeong, H. J., Lam, Y., and de Lumen, B. O. (2002). Barley lunasin suppresses ras-induced colony formation and inhibits core histone acetylation in mammalian cells. *J Agric Food Chem.* 50(21):5903-5908.
35. Kang, S. K., Cha, S. H. and Jeon, H. G. (2006). Curcumin-induced histone hypoacetylation enhances caspase-3-dependent glioma cell death and neurogenesis of neural progenitor cells. *Stem Cells Dev.* 15(2):165-74.
36. Krebbers, E., Herdies, L., DeClercq, A., Seurinck, J., Leemans, J., VanDamme, J., Segura, M., Gheysen, G., VanMontagu, M., and Vandekerckhove, J. (1988). Determination of the Processing Sites of an *Arabidopisis* 2S Albumin and Characterization of the Complete Gene Family. *Plant Physiol,* 81:859-866.
37. Lam, Y., Galvez, A., and de Lumen, B. O. (2003). Lunasin suppresses E1A-mediated transformation of mammalian cells but does not inhibit growth of immortalized and established cancer cell lines. *Nutr Cancer* 47(1):88-94.
38. Li, S., McGuire, M. J., Lin, M., Liu, Y-H., Oyama, T., Sun, X., and Brown, K. C. (2009). Synthesis and characterization of a high-affinitiy $\alpha_v\beta_6$-specific ligand for in vitro and in vivo applications. *Mol. Cancer. Ther.* 8(5):1239-48.
39. Lin, J., Fido, R., Shewry, P., Archer, D. B., Alcocer, M. J. C. (2004). The expression and processing of two recombinant 2S albumins from soybean (*Glycine max*) in the yeast *Pichia pastoris. Biochimica et Biophysica Acta* 1698:203-212.
40. Liu, C. F., and Pan, T. M. (2010). Recombinant expression of bioactive peptide lunasin in *Escherichia coli. Appl Microbiol Biotechnol.* 88:177-186.
41. Maldonado-Cervantes, E., Jeong, H. J., Leon-Galvan, F., Barrera-Pacheco, A., DeLeon-Rodriguez, A., de Mejia, E. G., deLumen, B. O., de la Rosa, A. P. B. (2010). Amaranth lunasin-like peptide internalizes into the cell nucleus and inhibits chemical carcinogen-induced transformation of NIH-3T3 cells. *Peptides.*
42. Martin, G. A., Kawaguchi, R., Lam, Y., DeGiovanni, A., Fukushima, M., and Mutter, W. (2001). High-yield, in vitro protein expression using a continuous-exchange, coupled transcription/translation system. *Biotechniques* 31(4):948-950, 952-3.
43. Odani, S., Koide, T., & Ono, T. (1987). Amino Acid Sequence of a Soybean (*Glycine max*) Seed Polypeptide Having a Poly(L-Aspartic Acid) Structure. *The Journal of Biological Chemistry* 262:10502-10505.
44. Omoni, A. O. and Aluko, R. E. (2005). Soybean Foods and Their Benefits: Potential Mechanisms of Action. *Nutrition Reviews.* 63(8):272-283.
45. Park, J. H., Jeong, H. J., and Lumen, B. O. (2007). In vitro digestibility of the cancer-preventive soy peptides lunasin and BBI. *J Agric Food Chem.* 55, 10703-10706.

46. Park, J. H., Jeong, H. J., and de Lumen, B. O. (2005). Contents and bioactivities of lunasin, bowman-birk inhibitor, and isoflavones in soybean seed. *J Agric Food Chem* 53:7686-7690.
47. Rodriguez, B. A. and Huang, T. H. (2005). Tilling the chromatin landscape: emerging methods for the discovery and profiling of protein-DNA interactions. *Biochem Cell Biol.* 83(4):525-34.
48. Silva-Sanchez, C., de la Rosa, A. P., Leon-Galvan, M. F., de Lumen, B. O., de Leon-Rodriguez, A., and de Mejia, E. G. (2008). Bioactive peptides in amaranth (*Amaranthus hypochondriacus*) seed. *J Agric Food Chem* 56(4):1233-1240.
49. Wang, W., Bringe, N. A., Berhow, M. A., and Gonzalez de Mejia, E. (2008a). beta-Conglycinins among sources of bioactives in hydrolysates of different soybean varieties that inhibit leukemia cells in vitro. *J Agric Food Chem.* 56(11):4012-4020.
50. Wang, W., Dia, V. P., Vasconez, M., de Mejia, E. G., and Nelson, R. L. (2008b). Analysis of soybean protein-derived peptides and the effect of cultivar, environmental conditions, and processing on lunasin concentration in soybean and soy products. *J AOAC Int* 91(4):936-946.
51. U.S. Pat. No. 7,731,995—Methods for using soy peptides to inhibit H3 acetylation, reduce expression of HMG CoA reductase, and increase LDL receptor and Sp1 expression in a mammal.
52. U.S. Pat. No. 7,404,973, Bowman-Birk inhibitor soy protein concentrate composition.
53. U.S. Pat. No. 7,375,092, Lunasin peptides.
54. U.S. Pat. No. 7,309,688, Topical anti-cancer compositions and methods of use thereof.
55. U.S. Pat. No. 7,192,615, Compositions containing legume products.
56. U.S. Pat. No. 6,544,956, Lunasin peptides.
57. U.S. Pat. No. 6,391,848, Soybean protein nutraceuticals.
58. U.S. Pat. No. 6,107,287, Lunasin peptides.
59. International Patent Application Publication No. WO/2001/034808 to Peters, Method of Large-Scale Production and Method of Testing of the Biological Activity of a Substance from Soybean.
60. U.S. Patent Application Publication No. 2010/0092497, Methods of Immune or Haematological Enhancement, Inhibiting Tumour Formation or Growth, and treating or Preventing Cancer.
61. U.S. Patent Application Publication No. 2010/0197594, Methods for Using Soy Peptides to Inhibit h3 Acetylation, Reduce Expression of hmg-coa reductase and Increase LDL Receptor and SP1 Expression in a Mammal.
62. U.S. Patent Application Publication No. 2008/0070827, Methods for Using Soy Peptides to Inhibit H3 Acetylation, Reduce Expression of hmg coa reductase, and Increase LDL Receptor and SP1 Expression in a Mammal.
63. U.S. Patent Application Publication No. 2008/0003567, Use of Lunasin Peptide as a Transcriptional Activator to Prevent Cancer and Related Methods for Treatment, Monitoring and Prognosis.
64. U.S. Patent Application Publication No. 2007/0292494, Carbohydrate-Derivatized Liposomes for Targeting Cellular Carbohydrate Recognition Domains of Ctl/Ctld Lectins, and Intracellular Delivery of Therapeutically Active Compounds.
65. U.S. Patent Application Publication No. 2007/0054031, Methods of extracting, concentrating and fractionating proteins and other chemical components.
66. U.S. Patent Application Publication No. 2003/0229038, Lunasin peptides.
67. U.S. Patent Application Publication No. 2003/0224420, Method for obtaining and measuring proliferation of long-term label retaining cells and stem cells.
68. U.S. Patent Application Publication No. 2003/0064121, High protein, Bowman-Birk Inhibitor Concentrate and process for its manufacture.
69. U.S. Patent Application Publication No. 2003/0027765, Therapeutic peptides having a motif that binds specifically to non-acetylated H3 and H4 histones for cancer therapy.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of purifying lunasin produced in a plant, comprising:
   (a) providing a plant material from the plant;
   (b) isolating a lunasin-containing complex from the plant material; and
   (c) contacting the lunasin-containing complex with another protein with a reducing agent, thereby releasing lunasin from the lunasin-containing complex.

2. The method of claim 1, wherein the plant is a soybean plant.

3. The method of claim 1, wherein the plant material is a soy-based material containing a lunasin-containing complex.

4. The method of claim 1, wherein the plant material is a soybean material obtained as a byproduct of soybean processing.

5. The method of claim 4, wherein the soybean material is de-fatted soy flour or white flake.

6. The method of claim 1, wherein the plant material is a hydrated plant material or an extracted plant material.

7. The method of claim 1, further comprising extracting the plant material.

8. The method of claim 7, wherein the plant material is extracted using water or an aqueous solution.

9. The method of claim 7, wherein the plant material is extracted using PBS.

10. The method of claim 1, wherein the reducing agent is selected form: β-mercaptoethanol (BME), dithiothreitol (DTT), tris(2-carboxyethyl)phosphine (TCEP), and 2-aminoethanethiol.

11. The method of claim 10, wherein the reducing agent is BME at a concentration of about 100 mM to about 1.5 M.

12. The method of claim 1, wherein the reducing agent is DTT at a concentration of about 1 mM to about 2 mM.

13. The method of claim 1, wherein the reducing agent is TCEP at a concentration of about 3 mM to about 100 mM.

14. The method of claim 1, further comprising purifying the released lunasin.

15. The method of claim 14, wherein the lunasin is purified using a technique selected from: a size-based filtration technique; a charge-based filtration technique; a hydrophobicity-based filtration technique; or a combination thereof.

16. The method of claim 1, wherein isolating the lunasin-containing complex comprises using a technique selected from: a size-based filtration technique; a charge-based filtration technique; a hydrophobicity-based filtration technique; or a combination thereof.

17. The method of claim 1, wherein isolating the lunasin-containing complex comprises subjecting the plant material to ultrafiltration and collecting the permeate.

18. The method of claim 17, wherein a 50 kD molecular-weight cutoff membrane is used for ultrafiltration.

* * * * *

SEQUENCE LISTING

```
<160> NUMBER OF SEQ ID NOS: 3

<210> SEQ ID NO 1
<211> LENGTH: 43
<212> TYPE: PRT
<213> ORGANISM: Glycine max

<400> SEQUENCE: 1

Ser Lys Trp Gln His Gln Gln Asp Ser Cys Arg Lys Gln Leu Gln Gly
1               5                   10                  15

Val Asn Leu Thr Pro Cys Glu Lys His Ile Met Glu Lys Ile Gln Gly
            20                  25                  30

Arg Gly Asp Asp Asp Asp Asp Asp Asp Asp
        35                  40

<210> SEQ ID NO 2
<211> LENGTH: 44
<212> TYPE: PRT
<213> ORGANISM: Glycine max

<400> SEQUENCE: 2
```

-continued

```
Ser Lys Trp Gln His Gln Gln Asp Ser Cys Arg Lys Gln Leu Gln Gly
1               5                   10                  15

Val Asn Leu Thr Pro Cys Glu Lys His Ile Met Glu Lys Ile Gln Gly
            20                  25                  30

Arg Gly Asp Asp Asp Asp Asp Asp Asp Asp Asn
        35                  40

<210> SEQ ID NO 3
<211> LENGTH: 77
<212> TYPE: PRT
<213> ORGANISM: Glycine max

<400> SEQUENCE: 3

Glu Gly Lys Asp Glu Asp Glu Glu Glu Gly His Met Gln Lys Cys
1               5                   10                  15

Cys Thr Glu Met Ser Glu Leu Arg Ser Pro Lys Cys Gln Cys Lys Ala
            20                  25                  30

Leu Gln Lys Ile Met Glu Asn Gln Ser Glu Glu Leu Glu Glu Lys Gln
            35                  40                  45

Lys Lys Lys Met Glu Lys Glu Leu Ile Asn Leu Ala Thr Met Cys Arg
        50                  55                  60

Phe Gly Pro Met Ile Gln Cys Asp Leu Ser Ser Asp Asp
65                  70                  75
```